(12) United States Patent
Roder et al.

(10) Patent No.: US 6,720,137 B2
(45) Date of Patent: Apr. 13, 2004

(54) **MICROSATELLITE MARKERS FOR PLANTS OF THE SPECIES *TRITICUM AESTIVUM* AND *TRIBE TRITICEAE* AND THE USE OF SAID MARKERS**

(75) Inventors: Marion Roder, Rieder (DE); Jens Plaschke, Meissen (DE); Martin Ganal, Rieder (DE)

(73) Assignee: Institut fur Pflanzengenetik und Kulturpflanzenforschung, Gatersleben (DE)

( * ) Notice: Subject to any disclaimer, the term of this patent is extended or adjusted under 35 U.S.C. 154(b) by 0 days.

(21) Appl. No.: 08/983,605

(22) PCT Filed: Jun. 27, 1996

(86) PCT No.: PCT/DE96/01185

§ 371 (c)(1),
(2), (4) Date: May 1, 1998

(87) PCT Pub. No.: WO97/01567

PCT Pub. Date: Jan. 16, 1997

(65) Prior Publication Data

US 2002/0066118 A1 May 30, 2002

(30) Foreign Application Priority Data

Jun. 28, 1995 (DE) .......................................... 195 25 284

(51) Int. Cl.[7] .......................... C12Q 1/68; C12P 19/34; C12N 5/00; C07H 21/02; A01H 11/00

(52) U.S. Cl. ...................... 435/6; 435/91.2; 435/320.1; 435/410; 536/23.1; 536/24.3; 536/24.33; 800/295; 800/320.3

(58) Field of Search .......................... 435/6, 91.2, 410, 435/320.1; 536/23.1, 24.3, 24.33; 800/295, 320.3

(56) References Cited

U.S. PATENT DOCUMENTS 5,332,408 A * 7/1994 Mets et al. ..................... 47/58
5,955,276 A * 9/1999 Morgante et al. .............. 435/6

OTHER PUBLICATIONS

Roder et al. Mol. Gen. Genet. vol. 246, No. 3, Feb. 6, 1995, p. 327–333.*

* cited by examiner

*Primary Examiner*—Gary Benzion
*Assistant Examiner*—Arun K Chakrabarti
(74) *Attorney, Agent, or Firm*—Norris McLaughlin & Marcus

(57) ABSTRACT

A set of a plurality of microsatellite markers is provided for plant species of the tribe Triticeae, particularly Triticum aestivum. Each of the markers are constituted by a sequence tagged site (STS) defined by two primers, specific to a particular microsatellite sequence. Each primer has an average length of 20±3 bases and flanks the particular microsatellite sequence. Each of the microsatellite markers is formed by amplification of the microsatellite sequence by a polymerase chain reaction, to form markers of different length.

3 Claims, No Drawings

SEQUENCE LISTING

<160> NUMBER OF SEQ ID NOS: 466

<210> SEQ ID NO 1
<211> LENGTH: 20
<212> TYPE: DNA
<213> ORGANISM: Triticum aestivum

<400> SEQUENCE: 1
ctatgaggcg gaggttgaag                    20

-continued

<210> SEQ ID NO 2
<211> LENGTH: 18
<212> TYPE: DNA
<213> ORGANISM: Triticum aestivum

<400> SEQUENCE: 2
tgcggtgctc ttccattt                                                    18

<210> SEQ ID NO 3
<211> LENGTH: 21
<212> TYPE: DNA
<213> ORGANISM: Triticum aestivum

<400> SEQUENCE: 3
gcatctggta cactagctgc c                                                21

<210> SEQ ID NO 4
<211> LENGTH: 20
<212> TYPE: DNA
<213> ORGANISM: Triticum aestivum

<400> SEQUENCE: 4
tcatggatgc atcacatcct                                                  20

<210> SEQ ID NO 5
<211> LENGTH: 21
<212> TYPE: DNA
<213> ORGANISM: Triticum aestivum

<400> SEQUENCE: 5
tcgattctga aaggttcatc g                                                21

<210> SEQ ID NO 6
<211> LENGTH: 21
<212> TYPE: DNA
<213> ORGANISM: Triticum aestivum

<400> SEQUENCE: 6
cgatcaagta gttgaaagcg c                                                21

<210> SEQ ID NO 7
<211> LENGTH: 21
<212> TYPE: DNA
<213> ORGANISM: Triticum aestivum

<400> SEQUENCE: 7
tctgatcccg tgagtgtaac a                                                21

<210> SEQ ID NO 8
<211> LENGTH: 22
<212> TYPE: DNA
<213> ORGANISM: Triticum aestivum

<400> SEQUENCE: 8
gaaaaaaatt gcatatgagc cc                                               22

<210> SEQ ID NO 9
<211> LENGTH: 19
<212> TYPE: DNA
<213> ORGANISM: Triticum aestivum

<400> SEQUENCE: 9
tgtcctacac ggaccacgt                                                   19

-continued

<210> SEQ ID NO 10
<211> LENGTH: 19
<212> TYPE: DNA
<213> ORGANISM: Triticum aestivum

<400> SEQUENCE: 10
gcattgacag atgcacacg                                                    19

<210> SEQ ID NO 11
<211> LENGTH: 18
<212> TYPE: DNA
<213> ORGANISM: Triticum aestivum

<400> SEQUENCE: 11
tcgacctgat cgcccta                                                      18

<210> SEQ ID NO 12
<211> LENGTH: 20
<212> TYPE: DNA
<213> ORGANISM: Triticum aestivum

<400> SEQUENCE: 12
cgccctgggt gatgaatagt                                                   20

<210> SEQ ID NO 13
<211> LENGTH: 21
<212> TYPE: DNA
<213> ORGANISM: Triticum aestivum

<400> SEQUENCE: 13
accacacaaa caaggtaagc g                                                 21

<210> SEQ ID NO 14
<211> LENGTH: 22
<212> TYPE: DNA
<213> ORGANISM: Triticum aestivum

<400> SEQUENCE: 14
caaccctctt aattttgttg gg                                                22

<210> SEQ ID NO 15
<211> LENGTH: 19
<212> TYPE: DNA
<213> ORGANISM: Triticum aestivum

<400> SEQUENCE: 15
aggccagaat ctgggaatg                                                    19

<210> SEQ ID NO 16
<211> LENGTH: 20
<212> TYPE: DNA
<213> ORGANISM: Triticum aestivum

<400> SEQUENCE: 16
ctccctagat gggagaaggg                                                   20

<210> SEQ ID NO 17
<211> LENGTH: 20
<212> TYPE: DNA
<213> ORGANISM: Triticum aestivum

<400> SEQUENCE: 17

```
agtggctggg agagtgtcat                                          20

<210> SEQ ID NO 18
<211> LENGTH: 18
<212> TYPE: DNA
<213> ORGANISM: Triticum aestivum

<400> SEQUENCE: 18
gcccattacc gaggacac                                            18

<210> SEQ ID NO 19
<211> LENGTH: 18
<212> TYPE: DNA
<213> ORGANISM: Triticum aestivum

<400> SEQUENCE: 19
ggcagagcag cgagactc                                            18

<210> SEQ ID NO 20
<211> LENGTH: 22
<212> TYPE: DNA
<213> ORGANISM: Triticum aestivum

<400> SEQUENCE: 20
caagtggagc attaggtaca cg                                       22

<210> SEQ ID NO 21
<211> LENGTH: 20
<212> TYPE: DNA
<213> ORGANISM: Triticum aestivum

<400> SEQUENCE: 21
acaaaggtaa gcagcacctg                                          20

<210> SEQ ID NO 22
<211> LENGTH: 18
<212> TYPE: DNA
<213> ORGANISM: Triticum aestivum

<400> SEQUENCE: 22
accctcttgc ccgtgttg                                            18

<210> SEQ ID NO 23
<211> LENGTH: 20
<212> TYPE: DNA
<213> ORGANISM: Triticum aestivum

<400> SEQUENCE: 23
acgttagaag gtgcaatggg                                          20

<210> SEQ ID NO 24
<211> LENGTH: 19
<212> TYPE: DNA
<213> ORGANISM: Triticum aestivum

<400> SEQUENCE: 24
agtggatgca ccgactttg                                           19

<210> SEQ ID NO 25
<211> LENGTH: 20
<212> TYPE: DNA
<213> ORGANISM: Triticum aestivum

<400> SEQUENCE: 25
```
cactacaact atgcgctcgc                                                 20

<210> SEQ ID NO 26
<211> LENGTH: 20
<212> TYPE: DNA
<213> ORGANISM: Triticum aestivum

<400> SEQUENCE: 26
tccattggct tctctctcaa                                                 20

<210> SEQ ID NO 27
<211> LENGTH: 20
<212> TYPE: DNA
<213> ORGANISM: Triticum aestivum

<400> SEQUENCE: 27
gatcaaacac acacccctcc                                                 20

<210> SEQ ID NO 28
<211> LENGTH: 20
<212> TYPE: DNA
<213> ORGANISM: Triticum aestivum

<400> SEQUENCE: 28
aatgcaaagt gaaaaacccg                                                 20

<210> SEQ ID NO 29
<211> LENGTH: 21
<212> TYPE: DNA
<213> ORGANISM: Triticum aestivum

<400> SEQUENCE: 29
aagatggacg tatgcatcac a                                               21

<210> SEQ ID NO 30
<211> LENGTH: 20
<212> TYPE: DNA
<213> ORGANISM: Triticum aestivum

<400> SEQUENCE: 30
gccatatttg atgacgcata                                                 20

<210> SEQ ID NO 31
<211> LENGTH: 18
<212> TYPE: DNA
<213> ORGANISM: Triticum aestivum

<400> SEQUENCE: 31
tctcccatcc aacgcctc                                                   18

<210> SEQ ID NO 32
<211> LENGTH: 20
<212> TYPE: DNA
<213> ORGANISM: Triticum aestivum

<400> SEQUENCE: 32
tgttggtggc ttgactattg                                                 20

<210> SEQ ID NO 33
<211> LENGTH: 20
<212> TYPE: DNA
<213> ORGANISM: Triticum aestivum

```
<210> SEQ ID NO 33
<211> LENGTH: 20
<212> TYPE: DNA
<213> ORGANISM: Triticum aestivum

<400> SEQUENCE: 33
ctgttcttgc gtggcattaa                                              20

<210> SEQ ID NO 34
<211> LENGTH: 22
<212> TYPE: DNA
<213> ORGANISM: Triticum aestivum

<400> SEQUENCE: 34
aataaggaca caattgggat gg                                           22

<210> SEQ ID NO 35
<211> LENGTH: 21
<212> TYPE: DNA
<213> ORGANISM: Triticum aestivum

<400> SEQUENCE: 35
attaatacct gagggaggtg c                                            21

<210> SEQ ID NO 36
<211> LENGTH: 20
<212> TYPE: DNA
<213> ORGANISM: Triticum aestivum

<400> SEQUENCE: 36
ggtctcagga gcaagaacac                                              20

<210> SEQ ID NO 37
<211> LENGTH: 20
<212> TYPE: DNA
<213> ORGANISM: Triticum aestivum

<400> SEQUENCE: 37
cgacaatggg gtcttagcat                                              20

<210> SEQ ID NO 38
<211> LENGTH: 22
<212> TYPE: DNA
<213> ORGANISM: Triticum aestivum

<400> SEQUENCE: 38
tgcacactta aattacatcc gc                                           22

<210> SEQ ID NO 39
<211> LENGTH: 21
<212> TYPE: DNA
<213> ORGANISM: Triticum aestivum

<400> SEQUENCE: 39
tctgtaggct ctctccgact g                                            21

<210> SEQ ID NO 40
<211> LENGTH: 20
<212> TYPE: DNA
<213> ORGANISM: Triticum aestivum

<400> SEQUENCE: 40
acctgatcag atcccactcg                                              20

<210> SEQ ID NO 41
<211> LENGTH: 19
<212> TYPE: DNA
<213> ORGANISM: Triticum aestivum
```

-continued

<210> SEQ ID NO 41
<211> LENGTH: 19
<212> TYPE: DNA
<213> ORGANISM: Triticum aestivum

<400> SEQUENCE: 41
ctaaacacga cagcggtgg                                                19

<210> SEQ ID NO 42
<211> LENGTH: 20
<212> TYPE: DNA
<213> ORGANISM: Triticum aestivum

<400> SEQUENCE: 42
gatatgtgag cagcggtcag                                               20

<210> SEQ ID NO 43
<211> LENGTH: 22
<212> TYPE: DNA
<213> ORGANISM: Triticum aestivum

<400> SEQUENCE: 43
attcgaggtt aggaggaaga gg                                            22

<210> SEQ ID NO 44
<211> LENGTH: 20
<212> TYPE: DNA
<213> ORGANISM: Triticum aestivum

<400> SEQUENCE: 44
gagggtcggc ctataagacc                                               20

<210> SEQ ID NO 45
<211> LENGTH: 22
<212> TYPE: DNA
<213> ORGANISM: Triticum aestivum

<400> SEQUENCE: 45
acaaacagaa aatcaaaacc cg                                            22

<210> SEQ ID NO 46
<211> LENGTH: 19
<212> TYPE: DNA
<213> ORGANISM: Triticum aestivum

<400> SEQUENCE: 46
atccatcgcc attggagtg                                                19

<210> SEQ ID NO 47
<211> LENGTH: 20
<212> TYPE: DNA
<213> ORGANISM: Triticum aestivum

<400> SEQUENCE: 47
gatgttgcca cttgagcatg                                               20

<210> SEQ ID NO 48
<211> LENGTH: 22
<212> TYPE: DNA
<213> ORGANISM: Triticum aestivum

<400> SEQUENCE: 48
gattagtcaa atggaacacc cc                                            22

<210> SEQ ID NO 49
<211> LENGTH: 22
<212> TYPE: DNA

<213> ORGANISM: Triticum aestivum

<400> SEQUENCE: 49
tgactaacat cctttgtcac gc          22

<210> SEQ ID NO 50
<211> LENGTH: 20
<212> TYPE: DNA
<213> ORGANISM: Triticum aestivum

<400> SEQUENCE: 50
catgtctcaa ccacccacag          20

<210> SEQ ID NO 51
<211> LENGTH: 20
<212> TYPE: DNA
<213> ORGANISM: Triticum aestivum

<400> SEQUENCE: 51
gatccacctt cctctctctc          20

<210> SEQ ID NO 52
<211> LENGTH: 20
<212> TYPE: DNA
<213> ORGANISM: Triticum aestivum

<400> SEQUENCE: 52
gattatactg gtgccgaaac          20

<210> SEQ ID NO 53
<211> LENGTH: 20
<212> TYPE: DNA
<213> ORGANISM: Triticum aestivum

<400> SEQUENCE: 53
tcctctacaa acaaacacac          20

<210> SEQ ID NO 54
<211> LENGTH: 20
<212> TYPE: DNA
<213> ORGANISM: Triticum aestivum

<400> SEQUENCE: 54
ctcgcaacta gaggtgtatg          20

<210> SEQ ID NO 55
<211> LENGTH: 19
<212> TYPE: DNA
<213> ORGANISM: Triticum aestivum

<400> SEQUENCE: 55
gggtgggaga aaggagatg          19

<210> SEQ ID NO 56
<211> LENGTH: 19
<212> TYPE: DNA
<213> ORGANISM: Triticum aestivum

<400> SEQUENCE: 56
aaaccatcct ccatcctgg          19

<210> SEQ ID NO 57
<211> LENGTH: 18

```
<212> TYPE: DNA
<213> ORGANISM: Triticum aestivum

<400> SEQUENCE: 57
gccatggcta tcacccag                                                   18

<210> SEQ ID NO 58
<211> LENGTH: 20
<212> TYPE: DNA
<213> ORGANISM: Triticum aestivum

<400> SEQUENCE: 58
actgttcggt gcaatttgag                                                 20

<210> SEQ ID NO 59
<211> LENGTH: 18
<212> TYPE: DNA
<213> ORGANISM: Triticum aestivum

<400> SEQUENCE: 59
cacacgctcc accatgac                                                   18

<210> SEQ ID NO 60
<211> LENGTH: 19
<212> TYPE: DNA
<213> ORGANISM: Triticum aestivum

<400> SEQUENCE: 60
gttgagttga tgcgggagg                                                  19

<210> SEQ ID NO 61
<211> LENGTH: 20
<212> TYPE: DNA
<213> ORGANISM: Triticum aestivum

<400> SEQUENCE: 61
agcacatttt aacacagata                                                 20

<210> SEQ ID NO 62
<211> LENGTH: 20
<212> TYPE: DNA
<213> ORGANISM: Triticum aestivum

<400> SEQUENCE: 62
atctgtgaaa ttttgaaaac                                                 20

<210> SEQ ID NO 63
<211> LENGTH: 20
<212> TYPE: DNA
<213> ORGANISM: Triticum aestivum

<400> SEQUENCE: 63
tcagtgggca agctacacag                                                 20

<210> SEQ ID NO 64
<211> LENGTH: 18
<212> TYPE: DNA
<213> ORGANISM: Triticum aestivum

<400> SEQUENCE: 64
aaaacttagt agccgcgt                                                   18

<210> SEQ ID NO 65
```

-continued

```
<211> LENGTH: 20
<212> TYPE: DNA
<213> ORGANISM: Triticum aestivum

<400> SEQUENCE: 65
agctctgctt cacgaggaag                                              20

<210> SEQ ID NO 66
<211> LENGTH: 21
<212> TYPE: DNA
<213> ORGANISM: Triticum aestivum

<400> SEQUENCE: 66 ctcctctttta tatcgcgtcc c                                           21

<210> SEQ ID NO 67
<211> LENGTH: 20
<212> TYPE: DNA
<213> ORGANISM: Triticum aestivum

<400> SEQUENCE: 67
aatccccacc gattcttctc                                              20

<210> SEQ ID NO 68
<211> LENGTH: 20
<212> TYPE: DNA
<213> ORGANISM: Triticum aestivum

<400> SEQUENCE: 68
agttcgtggg tctctgatgg                                              20

<210> SEQ ID NO 69
<211> LENGTH: 22
<212> TYPE: DNA
<213> ORGANISM: Triticum aestivum

<400> SEQUENCE: 69
taccaaatcg aaacacatca gg                                           22

<210> SEQ ID NO 70
<211> LENGTH: 21
<212> TYPE: DNA
<213> ORGANISM: Triticum aestivum

<400> SEQUENCE: 70
catatcaagg tctccttccc c                                            21

<210> SEQ ID NO 71
<211> LENGTH: 20
<212> TYPE: DNA
<213> ORGANISM: Triticum aestivum

<400> SEQUENCE: 71
atctaaacaa gacggcggtg                                              20

<210> SEQ ID NO 72
<211> LENGTH: 20
<212> TYPE: DNA
<213> ORGANISM: Triticum aestivum

<400> SEQUENCE: 72
atctgtgaca accggtgaga                                              20
```

-continued

<210> SEQ ID NO 73
<211> LENGTH: 21
<212> TYPE: DNA
<213> ORGANISM: Triticum aestivum

<400> SEQUENCE: 73
catggaactt agacagaatt g                                      21

<210> SEQ ID NO 74
<211> LENGTH: 21
<212> TYPE: DNA
<213> ORGANISM: Triticum aestivum

<400> SEQUENCE: 74
cagtacttgg tactgaacag g                                      21

<210> SEQ ID NO 75
<211> LENGTH: 22
<212> TYPE: DNA
<213> ORGANISM: Triticum aestivum

<400> SEQUENCE: 75
tgtcaacatc gttttgaaaa gg                                     22

<210> SEQ ID NO 76
<211> LENGTH: 20
<212> TYPE: DNA
<213> ORGANISM: Triticum aestivum

<400> SEQUENCE: 76
acactgtcaa cctggcaatg                                        20

<210> SEQ ID NO 77
<211> LENGTH: 19
<212> TYPE: DNA
<213> ORGANISM: Triticum aestivum

<400> SEQUENCE: 77
gacagcacct tgcccttttg                                         19

<210> SEQ ID NO 78
<211> LENGTH: 19
<212> TYPE: DNA
<213> ORGANISM: Triticum aestivum

<400> SEQUENCE: 78
catcggcaac atgctcatc                                          19

<210> SEQ ID NO 79
<211> LENGTH: 22
<212> TYPE: DNA
<213> ORGANISM: Triticum aestivum

<400> SEQUENCE: 79
atggagatat ttggcctaca ac                                      22

<210> SEQ ID NO 80
<211> LENGTH: 20
<212> TYPE: DNA
<213> ORGANISM: Triticum aestivum

<400> SEQUENCE: 80
cttgacttca aggcgtgaca                                         20

```
<210> SEQ ID NO 81
<211> LENGTH: 22
<212> TYPE: DNA
<213> ORGANISM: Triticum aestivum

<400> SEQUENCE: 81
tttgctgtgg tacgaaacat ac                                    22

<210> SEQ ID NO 82
<211> LENGTH: 22
<212> TYPE: DNA
<213> ORGANISM: Triticum aestivum

<400> SEQUENCE: 82
actcacaaat gtctaataaa ac                                    22

<210> SEQ ID NO 83
<211> LENGTH: 20
<212> TYPE: DNA
<213> ORGANISM: Triticum aestivum

<400> SEQUENCE: 83
ccaaaaaaac tgcctgcatg                                       20

<210> SEQ ID NO 84
<211> LENGTH: 19
<212> TYPE: DNA
<213> ORGANISM: Triticum aestivum

<400> SEQUENCE: 84
ctctggcatt gctccttgg                                        19

<210> SEQ ID NO 85
<211> LENGTH: 20
<212> TYPE: DNA
<213> ORGANISM: Triticum aestivum

<400> SEQUENCE: 85
gtgaggcagc aagagagaaa                                       20

<210> SEQ ID NO 86
<211> LENGTH: 21
<212> TYPE: DNA
<213> ORGANISM: Triticum aestivum

<400> SEQUENCE: 86
caaagcttga ctcagaccaa a                                     21

<210> SEQ ID NO 87
<211> LENGTH: 21
<212> TYPE: DNA
<213> ORGANISM: Triticum aestivum

<400> SEQUENCE: 87
cattgttttc tgcctctagc c                                     21

<210> SEQ ID NO 88
<211> LENGTH: 21
<212> TYPE: DNA
<213> ORGANISM: Triticum aestivum

<400> SEQUENCE: 88
ctagcatcga acctgaacaa g                                     21
```

-continued

<210> SEQ ID NO 89
<211> LENGTH: 20
<212> TYPE: DNA
<213> ORGANISM: Triticum aestivum

<400> SEQUENCE: 89
gatctcgtca cccggaattc                    20

<210> SEQ ID NO 90
<211> LENGTH: 20
<212> TYPE: DNA
<213> ORGANISM: Triticum aestivum

<400> SEQUENCE: 90
tggtagagaa ggacggagag                    20

<210> SEQ ID NO 91
<211> LENGTH: 20
<212> TYPE: DNA
<213> ORGANISM: Triticum aestivum

<400> SEQUENCE: 91
tcacagagag agagggaggg                    20

<210> SEQ ID NO 92
<211> LENGTH: 20
<212> TYPE: DNA
<213> ORGANISM: Triticum aestivum

<400> SEQUENCE: 92
atgtgtacat gttgcctgca                    20

<210> SEQ ID NO 93
<211> LENGTH: 18
<212> TYPE: DNA
<213> ORGANISM: Triticum aestivum

<400> SEQUENCE: 93
caatcatttc ccctccc                       18

<210> SEQ ID NO 94
<211> LENGTH: 22
<212> TYPE: DNA
<213> ORGANISM: Triticum aestivum

<400> SEQUENCE: 94
aatcattgga aatccatatg cc                 22

<210> SEQ ID NO 95
<211> LENGTH: 22
<212> TYPE: DNA
<213> ORGANISM: Triticum aestivum

<400> SEQUENCE: 95
ccaaccgtgc tattagtcat tc                 22

<210> SEQ ID NO 96
<211> LENGTH: 19
<212> TYPE: DNA
<213> ORGANISM: Triticum aestivum

<400> SEQUENCE: 96

-continued

| | |
|---|---|
| caatgcaggc cctcctaac | 19 |

<210> SEQ ID NO 97
<211> LENGTH: 18
<212> TYPE: DNA
<213> ORGANISM: Triticum aestivum

<400> SEQUENCE: 97

| | |
|---|---|
| gtcgtcgcgg taagcttg | 18 |

<210> SEQ ID NO 98
<211> LENGTH: 20
<212> TYPE: DNA
<213> ORGANISM: Triticum aestivum

<400> SEQUENCE: 98

| | |
|---|---|
| gagtgaacac acgaggcttg | 20 |

<210> SEQ ID NO 99
<211> LENGTH: 18
<212> TYPE: DNA
<213> ORGANISM: Triticum aestivum

<400> SEQUENCE: 99

| | |
|---|---|
| gggccaacac tggaacac | 18 |

<210> SEQ ID NO 100
<211> LENGTH: 20
<212> TYPE: DNA
<213> ORGANISM: Triticum aestivum

<400> SEQUENCE: 100

| | |
|---|---|
| gcagaagctt gttggtaggc | 20 |

<210> SEQ ID NO 101
<211> LENGTH: 21
<212> TYPE: DNA
<213> ORGANISM: Triticum aestivum

<400> SEQUENCE: 101

| | |
|---|---|
| ttcaattcag tcttggcttg g | 21 |

<210> SEQ ID NO 102
<211> LENGTH: 22
<212> TYPE: DNA
<213> ORGANISM: Triticum aestivum

<400> SEQUENCE: 102

| | |
|---|---|
| ctgcaggaaa aaagtacac cc | 22 |

<210> SEQ ID NO 103
<211> LENGTH: 20
<212> TYPE: DNA
<213> ORGANISM: Triticum aestivum

<400> SEQUENCE: 103

| | |
|---|---|
| gatcgagtga tggcagatgg | 20 |

<210> SEQ ID NO 104
<211> LENGTH: 20
<212> TYPE: DNA
<213> ORGANISM: Triticum aestivum

<400> SEQUENCE: 104

```
tgtgaattac ttggacgtgg                                              20

<210> SEQ ID NO 105
<211> LENGTH: 20
<212> TYPE: DNA
<213> ORGANISM: Triticum aestivum

<400> SEQUENCE: 105
agtggatcga caaggctctg                                              20

<210> SEQ ID NO 106
<211> LENGTH: 20
<212> TYPE: DNA
<213> ORGANISM: Triticum aestivum

<400> SEQUENCE: 106
agaagaagca aagccttccc                                              20

<210> SEQ ID NO 107
<211> LENGTH: 20
<212> TYPE: DNA
<213> ORGANISM: Triticum aestivum

<400> SEQUENCE: 107
acctcgacag acctggtacg                                              20

<210> SEQ ID NO 108
<211> LENGTH: 20
<212> TYPE: DNA
<213> ORGANISM: Triticum aestivum

<400> SEQUENCE: 108
gtctttgtca cccgatggac                                              20

<210> SEQ ID NO 109
<211> LENGTH: 19
<212> TYPE: DNA
<213> ORGANISM: Triticum aestivum

<400> SEQUENCE: 109
acatttctcc cccatcgtc                                               19

<210> SEQ ID NO 110
<211> LENGTH: 20
<212> TYPE: DNA
<213> ORGANISM: Triticum aestivum

<400> SEQUENCE: 110
ttgtaaacaa atcgcatgcg                                              20

<210> SEQ ID NO 111
<211> LENGTH: 20
<212> TYPE: DNA
<213> ORGANISM: Triticum aestivum

<400> SEQUENCE: 111
tgcagtggtc agatgtttcc                                              20

<210> SEQ ID NO 112
<211> LENGTH: 20
<212> TYPE: DNA
<213> ORGANISM: Triticum aestivum
```

-continued

```
<400> SEQUENCE: 112
cttttctttc agattgcgcc                                              20

<210> SEQ ID NO 113
<211> LENGTH: 22
<212> TYPE: DNA
<213> ORGANISM: Triticum aestivum

<400> SEQUENCE: 113
accactgcag agaacacata cg                                           22

<210> SEQ ID NO 114
<211> LENGTH: 21
<212> TYPE: DNA
<213> ORGANISM: Triticum aestivum

<400> SEQUENCE: 114
gtgctctgct ctaagtgtgg g                                            21

<210> SEQ ID NO 115
<211> LENGTH: 22
<212> TYPE: DNA
<213> ORGANISM: Triticum aestivum

<400> SEQUENCE: 115
gggttcctat ctggtaaatc cc                                           22

<210> SEQ ID NO 116
<211> LENGTH: 20
<212> TYPE: DNA
<213> ORGANISM: Triticum aestivum

<400> SEQUENCE: 116
gacacacatg ttcctgccac                                              20

<210> SEQ ID NO 117
<211> LENGTH: 20
<212> TYPE: DNA
<213> ORGANISM: Triticum aestivum

<400> SEQUENCE: 117
aagttgagtt gatgcgggag                                              20

<210> SEQ ID NO 118
<211> LENGTH: 19
<212> TYPE: DNA
<213> ORGANISM: Triticum aestivum

<400> SEQUENCE: 118
ccatgaccag catccactc                                               19

<210> SEQ ID NO 119
<211> LENGTH: 20
<212> TYPE: DNA
<213> ORGANISM: Triticum aestivum

<400> SEQUENCE: 119
atccgcctaa ggaatagtgt                                              20

<210> SEQ ID NO 120
<211> LENGTH: 19
<212> TYPE: DNA
<213> ORGANISM: Triticum aestivum
```

<400> SEQUENCE: 120
gatcgcacgg gagagagag                                                19

<210> SEQ ID NO 121
<211> LENGTH: 20
<212> TYPE: DNA
<213> ORGANISM: Triticum aestivum

<400> SEQUENCE: 121
tcattggtaa tgaggagaga                                               20

<210> SEQ ID NO 122
<211> LENGTH: 20
<212> TYPE: DNA
<213> ORGANISM: Triticum aestivum

<400> SEQUENCE: 122
gaaccattca tgtgcatgtc                                               20

<210> SEQ ID NO 123
<211> LENGTH: 21
<212> TYPE: DNA
<213> ORGANISM: Triticum aestivum

<400> SEQUENCE: 123
tgatgtagtg agcccatagg c                                             21

<210> SEQ ID NO 124
<211> LENGTH: 20
<212> TYPE: DNA
<213> ORGANISM: Triticum aestivum

<400> SEQUENCE: 124
ttgcacacag ccaaataagg                                               20

<210> SEQ ID NO 125
<211> LENGTH: 20
<212> TYPE: DNA
<213> ORGANISM: Triticum aestivum

<400> SEQUENCE: 125
gcagagcctg gttcaaaaag                                               20

<210> SEQ ID NO 126
<211> LENGTH: 20
<212> TYPE: DNA
<213> ORGANISM: Triticum aestivum

<400> SEQUENCE: 126
cgcctctagc gagagctatg                                               20

<210> SEQ ID NO 127
<211> LENGTH: 18
<212> TYPE: DNA
<213> ORGANISM: Triticum aestivum

<400> SEQUENCE: 127
aggagcagcg gaacgaac                                                 18

<210> SEQ ID NO 128
<211> LENGTH: 20
<212> TYPE: DNA

<213> ORGANISM: Triticum aestivum

<400> SEQUENCE: 128
agaaatacgg aaacccaccc					20

<210> SEQ ID NO 129
<211> LENGTH: 21
<212> TYPE: DNA
<213> ORGANISM: Triticum aestivum

<400> SEQUENCE: 129
gtgcttgctg agctatgagt c					21

<210> SEQ ID NO 130
<211> LENGTH: 19
<212> TYPE: DNA
<213> ORGANISM: Triticum aestivum

<400> SEQUENCE: 130
gtgccacgtg gtacctttg					19

<210> SEQ ID NO 131
<211> LENGTH: 18
<212> TYPE: DNA
<213> ORGANISM: Triticum aestivum

<400> SEQUENCE: 131
agactgttgt ttgcgggc					18

<210> SEQ ID NO 132
<211> LENGTH: 22
<212> TYPE: DNA
<213> ORGANISM: Triticum aestivum

<400> SEQUENCE: 132
tagcacgaca gttgtatgca tg				22

<210> SEQ ID NO 133
<211> LENGTH: 20
<212> TYPE: DNA
<213> ORGANISM: Triticum aestivum

<400> SEQUENCE: 133
ggttttcttt cagattgcgc					20

<210> SEQ ID NO 134
<211> LENGTH: 21
<212> TYPE: DNA
<213> ORGANISM: Triticum aestivum

<400> SEQUENCE: 134
cgttgtctaa tcttgccttg c					21

<210> SEQ ID NO 135
<211> LENGTH: 20
<212> TYPE: DNA
<213> ORGANISM: Triticum aestivum

<400> SEQUENCE: 135
ctttgtgcac ctctctctcc					20

<210> SEQ ID NO 136
<211> LENGTH: 21

```
<212> TYPE: DNA
<213> ORGANISM: Triticum aestivum

<400> SEQUENCE: 136
aattgtgttg atgatttggg g                                      21

<210> SEQ ID NO 137
<211> LENGTH: 20
<212> TYPE: DNA
<213> ORGANISM: Triticum aestivum

<400> SEQUENCE: 137
gatctgctct actctcctcc                                        20

<210> SEQ ID NO 138
<211> LENGTH: 20
<212> TYPE: DNA
<213> ORGANISM: Triticum aestivum

<400> SEQUENCE: 138
cgacgcagaa cttaaacaag                                        20

<210> SEQ ID NO 139
<211> LENGTH: 18
<212> TYPE: DNA
<213> ORGANISM: Triticum aestivum

<400> SEQUENCE: 139
aggtgccgtc gcgtctac                                          18

<210> SEQ ID NO 140
<211> LENGTH: 18
<212> TYPE: DNA
<213> ORGANISM: Triticum aestivum

<400> SEQUENCE: 140
accccccacg tcagagag                                          18

<210> SEQ ID NO 141
<211> LENGTH: 21
<212> TYPE: DNA
<213> ORGANISM: Triticum aestivum

<400> SEQUENCE: 141
gagaaagagg tctggaggtc g                                      21

<210> SEQ ID NO 142
<211> LENGTH: 21
<212> TYPE: DNA
<213> ORGANISM: Triticum aestivum

<400> SEQUENCE: 142
caaaatgcac aagaatggag g                                      21

<210> SEQ ID NO 143
<211> LENGTH: 20
<212> TYPE: DNA
<213> ORGANISM: Triticum aestivum

<400> SEQUENCE: 143
ttgaaccgga aggagtacag                                        20

<210> SEQ ID NO 144
```

```
<211> LENGTH: 21
<212> TYPE: DNA
<213> ORGANISM: Triticum aestivum

<400> SEQUENCE: 144
tcagtttatt tgggcatgt g                                           21

<210> SEQ ID NO 145
<211> LENGTH: 19
<212> TYPE: DNA
<213> ORGANISM: Triticum aestivum

<400> SEQUENCE: 145
tcaacggaac agatgagcg                                             19

<210> SEQ ID NO 146
<211> LENGTH: 20
<212> TYPE: DNA
<213> ORGANISM: Triticum aestivum

<400> SEQUENCE: 146
gacctgatga gagcaagcac                                            20

<210> SEQ ID NO 147
<211> LENGTH: 17
<212> TYPE: DNA
<213> ORGANISM: Triticum aestivum

<400> SEQUENCE: 147
cccaaagcag cgcaagc                                               17

<210> SEQ ID NO 148
<211> LENGTH: 18
<212> TYPE: DNA
<213> ORGANISM: Triticum aestivum

<400> SEQUENCE: 148
accaatgcta tcggctcg                                              18

<210> SEQ ID NO 149
<211> LENGTH: 18
<212> TYPE: DNA
<213> ORGANISM: Triticum aestivum

<400> SEQUENCE: 149
cgacccggtt cacttcag                                              18

<210> SEQ ID NO 150
<211> LENGTH: 20
<212> TYPE: DNA
<213> ORGANISM: Triticum aestivum

<400> SEQUENCE: 150
agtcgccgtt gtatagtgcc                                            20

<210> SEQ ID NO 151
<211> LENGTH: 22
<212> TYPE: DNA
<213> ORGANISM: Triticum aestivum

<400> SEQUENCE: 151
tgcatcaaga atagtgtgga ag                                         22
```

-continued

```
<210> SEQ ID NO 152
<211> LENGTH: 20
<212> TYPE: DNA
<213> ORGANISM: Triticum aestivum

<400> SEQUENCE: 152
tgagaggaag gctcacacct                                                   20

<210> SEQ ID NO 153
<211> LENGTH: 20
<212> TYPE: DNA
<213> ORGANISM: Triticum aestivum

<400> SEQUENCE: 153
aagcaacatt tgctgcaatg                                                   20

<210> SEQ ID NO 154
<211> LENGTH: 22
<212> TYPE: DNA
<213> ORGANISM: Triticum aestivum

<400> SEQUENCE: 154
tgcagttaac ttgttgaaag ga                                                22

<210> SEQ ID NO 155
<211> LENGTH: 20
<212> TYPE: DNA
<213> ORGANISM: Triticum aestivum

<400> SEQUENCE: 155
tgcctggctc gttctatctc                                                   20

<210> SEQ ID NO 156
<211> LENGTH: 20
<212> TYPE: DNA
<213> ORGANISM: Triticum aestivum

<400> SEQUENCE: 156
ctagcttagc actgtcgccc                                                   20

<210> SEQ ID NO 157
<211> LENGTH: 18
<212> TYPE: DNA
<213> ORGANISM: Triticum aestivum

<400> SEQUENCE: 157
cggcaaacgg atatcgac                                                     18

<210> SEQ ID NO 158
<211> LENGTH: 22
<212> TYPE: DNA
<213> ORGANISM: Triticum aestivum

<400> SEQUENCE: 158
aacagtaact ctcgccatag cc                                                22

<210> SEQ ID NO 159
<211> LENGTH: 20
<212> TYPE: DNA
<213> ORGANISM: Triticum aestivum

<400> SEQUENCE: 159
gatgagcgac acctagcctc                                                   20
```

<210> SEQ ID NO 160
<211> LENGTH: 18
<212> TYPE: DNA
<213> ORGANISM: Triticum aestivum

<400> SEQUENCE: 160
ggggtccgag tccacaac                                                    18

<210> SEQ ID NO 161
<211> LENGTH: 18
<212> TYPE: DNA
<213> ORGANISM: Triticum aestivum

<400> SEQUENCE: 161
tgagtccagc actgctgc                                                    18

<210> SEQ ID NO 162
<211> LENGTH: 20
<212> TYPE: DNA
<213> ORGANISM: Triticum aestivum

<400> SEQUENCE: 162
caacatccgc tcgtattcaa                                                  20

<210> SEQ ID NO 163
<211> LENGTH: 22
<212> TYPE: DNA
<213> ORGANISM: Triticum aestivum

<400> SEQUENCE: 163
tcatatgcac ctctttccta gg                                               22

<210> SEQ ID NO 164
<211> LENGTH: 19
<212> TYPE: DNA
<213> ORGANISM: Triticum aestivum

<400> SEQUENCE: 164
gtgtgccacc tttgacgtc                                                   19

<210> SEQ ID NO 165
<211> LENGTH: 18
<212> TYPE: DNA
<213> ORGANISM: Triticum aestivum

<400> SEQUENCE: 165
agctcgggat gaagcgtg                                                    18

<210> SEQ ID NO 166
<211> LENGTH: 17
<212> TYPE: DNA
<213> ORGANISM: Triticum aestivum

<400> SEQUENCE: 166
gatccgccgc tgcgttt                                                     17

<210> SEQ ID NO 167
<211> LENGTH: 17
<212> TYPE: DNA
<213> ORGANISM: Triticum aestivum

<400> SEQUENCE: 167
atctcaacgg caagccg                                                     17

<210> SEQ ID NO 168
<211> LENGTH: 19
<212> TYPE: DNA
<213> ORGANISM: Triticum aestivum

<400> SEQUENCE: 168
ctgatgcaag caatccacc                                                    19

<210> SEQ ID NO 169
<211> LENGTH: 23
<212> TYPE: DNA
<213> ORGANISM: Triticum aestivum

<400> SEQUENCE: 169
tcaaaacata aatgttcatt gga                                               23

<210> SEQ ID NO 170
<211> LENGTH: 22
<212> TYPE: DNA
<213> ORGANISM: Triticum aestivum

<400> SEQUENCE: 170
tcaaccgtgt gtaattttgt cc                                                22

<210> SEQ ID NO 171
<211> LENGTH: 22
<212> TYPE: DNA
<213> ORGANISM: Triticum aestivum

<400> SEQUENCE: 171
gagtcctgat gtgaagctgt tg                                                22

<210> SEQ ID NO 172
<211> LENGTH: 20
<212> TYPE: DNA
<213> ORGANISM: Triticum aestivum

<400> SEQUENCE: 172
ctcattgggg tgtgtacgtg                                                   20

<210> SEQ ID NO 173
<211> LENGTH: 22
<212> TYPE: DNA
<213> ORGANISM: Triticum aestivum

<400> SEQUENCE: 173
gaatcacttg tgaagcatct gg                                                22

<210> SEQ ID NO 174
<211> LENGTH: 20
<212> TYPE: DNA
<213> ORGANISM: Triticum aestivum

<400> SEQUENCE: 174
ctggatgcat cacatccaac                                                   20

<210> SEQ ID NO 175
<211> LENGTH: 18
<212> TYPE: DNA
<213> ORGANISM: Triticum aestivum

<400> SEQUENCE: 175

```
tcgcttctac cgctcacc                                          18

<210> SEQ ID NO 176
<211> LENGTH: 17
<212> TYPE: DNA
<213> ORGANISM: Triticum aestivum

<400> SEQUENCE: 176
agtgccttgc cgaggtc                                           17

<210> SEQ ID NO 177
<211> LENGTH: 20
<212> TYPE: DNA
<213> ORGANISM: Triticum aestivum

<400> SEQUENCE: 177
tcttccaact aaagcatagc                                        20

<210> SEQ ID NO 178
<211> LENGTH: 22
<212> TYPE: DNA
<213> ORGANISM: Triticum aestivum

<400> SEQUENCE: 178
cttccatgga ctacatacta gc                                     22

<210> SEQ ID NO 179
<211> LENGTH: 18
<212> TYPE: DNA
<213> ORGANISM: Triticum aestivum

<400> SEQUENCE: 179
tccaaggcag taggcagg                                          18

<210> SEQ ID NO 180
<211> LENGTH: 20
<212> TYPE: DNA
<213> ORGANISM: Triticum aestivum

<400> SEQUENCE: 180
tgttgttggc ctgtatgcat                                        20

<210> SEQ ID NO 181
<211> LENGTH: 18
<212> TYPE: DNA
<213> ORGANISM: Triticum aestivum

<400> SEQUENCE: 181
ggcagctgag gcaatctg                                          18

<210> SEQ ID NO 182
<211> LENGTH: 18
<212> TYPE: DNA
<213> ORGANISM: Triticum aestivum

<400> SEQUENCE: 182
tttggacatt tcccagcg                                          18

<210> SEQ ID NO 183
<211> LENGTH: 17
<212> TYPE: DNA
<213> ORGANISM: Triticum aestivum

<400> SEQUENCE: 183
```

```
cagcgcagtt agctcgc                                                    17

<210> SEQ ID NO 184
<211> LENGTH: 18
<212> TYPE: DNA
<213> ORGANISM: Triticum aestivum

<400> SEQUENCE: 184
atctgtccat tcgagcgc                                                   18

<210> SEQ ID NO 185
<211> LENGTH: 21
<212> TYPE: DNA
<213> ORGANISM: Triticum aestivum

<400> SEQUENCE: 185
gcaatctttt ttctgaccac g                                               21

<210> SEQ ID NO 186
<211> LENGTH: 17
<212> TYPE: DNA
<213> ORGANISM: Triticum aestivum

<400> SEQUENCE: 186
atgtgcatgt cggacgc                                                    17

<210> SEQ ID NO 187
<211> LENGTH: 17
<212> TYPE: DNA
<213> ORGANISM: Triticum aestivum

<400> SEQUENCE: 187
aggacttccg caccctg                                                    17

<210> SEQ ID NO 188
<211> LENGTH: 19
<212> TYPE: DNA
<213> ORGANISM: Triticum aestivum

<400> SEQUENCE: 188
tggcgtggtc taaatggac                                                  19

<210> SEQ ID NO 189
<211> LENGTH: 20
<212> TYPE: DNA
<213> ORGANISM: Triticum aestivum

<400> SEQUENCE: 189
caaatggatc gagaaaggga                                                 20

<210> SEQ ID NO 190
<211> LENGTH: 22
<212> TYPE: DNA
<213> ORGANISM: Triticum aestivum

<400> SEQUENCE: 190
ctgccatttt tctggatcta cc                                              22

<210> SEQ ID NO 191
<211> LENGTH: 21
<212> TYPE: DNA
<213> ORGANISM: Triticum aestivum
```

-continued

<400> SEQUENCE: 191
caactggttg ctacacaagc a                                              21

<210> SEQ ID NO 192
<211> LENGTH: 21
<212> TYPE: DNA
<213> ORGANISM: Triticum aestivum

<400> SEQUENCE: 192
gggatgtctg ttccatctta g                                              21

<210> SEQ ID NO 193
<211> LENGTH: 23
<212> TYPE: DNA
<213> ORGANISM: Triticum aestivum

<400> SEQUENCE: 193
caactgtacg taggtttcat tgc                                            23

<210> SEQ ID NO 194
<211> LENGTH: 18
<212> TYPE: DNA
<213> ORGANISM: Triticum aestivum

<400> SEQUENCE: 194
tctgccgtaa gtcgcctc                                                  18

<210> SEQ ID NO 195
<211> LENGTH: 18
<212> TYPE: DNA
<213> ORGANISM: Triticum aestivum

<400> SEQUENCE: 195
agagtgcatg gtgggacg                                                  18

<210> SEQ ID NO 196
<211> LENGTH: 20
<212> TYPE: DNA
<213> ORGANISM: Triticum aestivum

<400> SEQUENCE: 196
ccaagacgat gctgaagtca                                                20

<210> SEQ ID NO 197
<211> LENGTH: 22
<212> TYPE: DNA
<213> ORGANISM: Triticum aestivum

<400> SEQUENCE: 197
gatcgcttca tctctctctc tc                                             22

<210> SEQ ID NO 198
<211> LENGTH: 17
<212> TYPE: DNA
<213> ORGANISM: Triticum aestivum

<400> SEQUENCE: 198
gtacacgccg taggccc                                                   17

<210> SEQ ID NO 199
<211> LENGTH: 23
<212> TYPE: DNA
<213> ORGANISM: Triticum aestivum

```
<400> SEQUENCE: 199
agggaaaaga catctttttt ttc                                          23

<210> SEQ ID NO 200
<211> LENGTH: 17
<212> TYPE: DNA
<213> ORGANISM: Triticum aestivum

<400> SEQUENCE: 200
cgaccgactt cgggttc                                                 17

<210> SEQ ID NO 201
<211> LENGTH: 17
<212> TYPE: DNA
<213> ORGANISM: Triticum aestivum

<400> SEQUENCE: 201 gccccttgc acaaatc                                                  17

<210> SEQ ID NO 202
<211> LENGTH: 17
<212> TYPE: DNA
<213> ORGANISM: Triticum aestivum

<400> SEQUENCE: 202
cgcagctaca ggaggcc                                                 17

<210> SEQ ID NO 203
<211> LENGTH: 19
<212> TYPE: DNA
<213> ORGANISM: Triticum aestivum

<400> SEQUENCE: 203
ctccctgtac gcctaaggc                                               19

<210> SEQ ID NO 204
<211> LENGTH: 19
<212> TYPE: DNA
<213> ORGANISM: Triticum aestivum

<400> SEQUENCE: 204
ctcgcgctac tagccattg                                               19

<210> SEQ ID NO 205
<211> LENGTH: 18
<212> TYPE: DNA
<213> ORGANISM: Triticum aestivum

<400> SEQUENCE: 205
tctgccgtaa gtcgcctc                                                18

<210> SEQ ID NO 206
<211> LENGTH: 20
<212> TYPE: DNA
<213> ORGANISM: Triticum aestivum

<400> SEQUENCE: 206
ggtttcattg cttgccctaa                                              20

<210> SEQ ID NO 207
<211> LENGTH: 20
<212> TYPE: DNA
```

<213> ORGANISM: Triticum aestivum

<400> SEQUENCE: 207
gagaaacatg ccgaacaaca                                                    20

<210> SEQ ID NO 208
<211> LENGTH: 22
<212> TYPE: DNA
<213> ORGANISM: Triticum aestivum

<400> SEQUENCE: 208
gcatgcatga gaataggaac tg                                                 22

<210> SEQ ID NO 209
<211> LENGTH: 20
<212> TYPE: DNA
<213> ORGANISM: Triticum aestivum

<400> SEQUENCE: 209
tgttgcggat ggtcactatt                                                    20

<210> SEQ ID NO 210
<211> LENGTH: 21
<212> TYPE: DNA
<213> ORGANISM: Triticum aestivum

<400> SEQUENCE: 210
gagtacacat ttggcctctg c                                                  21

<210> SEQ ID NO 211
<211> LENGTH: 21
<212> TYPE: DNA
<213> ORGANISM: Triticum aestivum

<400> SEQUENCE: 211 agggatatg ttgtcactcc a                                                   21

<210> SEQ ID NO 212
<211> LENGTH: 22
<212> TYPE: DNA
<213> ORGANISM: Triticum aestivum

<400> SEQUENCE: 212
ttatgtgatt gcgtacgtac cc                                                 22

<210> SEQ ID NO 213
<211> LENGTH: 23
<212> TYPE: DNA
<213> ORGANISM: Triticum aestivum

<400> SEQUENCE: 213
tgcatataaa cagtcacaca ccc                                                23

<210> SEQ ID NO 214
<211> LENGTH: 23
<212> TYPE: DNA
<213> ORGANISM: Triticum aestivum

<400> SEQUENCE: 214
tttgagctcc aaagtgagtt agc                                                23

<210> SEQ ID NO 215
<211> LENGTH: 18

-continued

```
<212> TYPE: DNA
<213> ORGANISM: Triticum aestivum

<400> SEQUENCE: 215
caagatcgtg gagccagc                                                        18

<210> SEQ ID NO 216
<211> LENGTH: 20
<212> TYPE: DNA
<213> ORGANISM: Triticum aestivum

<400> SEQUENCE: 216
agctgctagc ttttgggaca                                                      20

<210> SEQ ID NO 217
<211> LENGTH: 21
<212> TYPE: DNA
<213> ORGANISM: Triticum aestivum

<400> SEQUENCE: 217
tgctctttgg cgaatatatg g                                                    21

<210> SEQ ID NO 218
<211> LENGTH: 23
<212> TYPE: DNA
<213> ORGANISM: Triticum aestivum

<400> SEQUENCE: 218
gttcaaaaca aattaaaagg ccc                                                  23

<210> SEQ ID NO 219
<211> LENGTH: 20
<212> TYPE: DNA
<213> ORGANISM: Triticum aestivum

<400> SEQUENCE: 219
attggacgga cagatgcttt                                                      20

<210> SEQ ID NO 220
<211> LENGTH: 19
<212> TYPE: DNA
<213> ORGANISM: Triticum aestivum

<400> SEQUENCE: 220
agcagtgagg aagggatc                                                        19

<210> SEQ ID NO 221
<211> LENGTH: 20
<212> TYPE: DNA
<213> ORGANISM: Triticum aestivum

<400> SEQUENCE: 221
aacttgcaaa actgttctga                                                      20

<210> SEQ ID NO 222
<211> LENGTH: 20
<212> TYPE: DNA
<213> ORGANISM: Triticum aestivum

<400> SEQUENCE: 222
tatttgaagc ggtttgattt                                                      20

<210> SEQ ID NO 223
```

```
<211> LENGTH: 22
<212> TYPE: DNA
<213> ORGANISM: Triticum aestivum

<400> SEQUENCE: 223
aattttcttc ctcacttatt ct                                              22

<210> SEQ ID NO 224
<211> LENGTH: 17
<212> TYPE: DNA
<213> ORGANISM: Triticum aestivum

<400> SEQUENCE: 224
aacaaaaaat tagggcc                                                    17

<210> SEQ ID NO 225
<211> LENGTH: 20
<212> TYPE: DNA
<213> ORGANISM: Triticum aestivum

<400> SEQUENCE: 225
atttgcctga agaaaatatt                                                 20

<210> SEQ ID NO 226
<211> LENGTH: 20
<212> TYPE: DNA
<213> ORGANISM: Triticum aestivum

<400> SEQUENCE: 226
aatttcactg catacacaag                                                 20

<210> SEQ ID NO 227
<211> LENGTH: 20
<212> TYPE: DNA
<213> ORGANISM: Triticum aestivum

<400> SEQUENCE: 227
gttgcttcat gaacgctcaa                                                 20

<210> SEQ ID NO 228
<211> LENGTH: 20
<212> TYPE: DNA
<213> ORGANISM: Triticum aestivum

<400> SEQUENCE: 228
ctgcccaatt ttctccactc                                                 20

<210> SEQ ID NO 229
<211> LENGTH: 23
<212> TYPE: DNA
<213> ORGANISM: Triticum aestivum

<400> SEQUENCE: 229
cggccatatt tctgtaagta tgc                                             23

<210> SEQ ID NO 230
<211> LENGTH: 17
<212> TYPE: DNA
<213> ORGANISM: Triticum aestivum

<400> SEQUENCE: 230
gcaggtaatg gccggac                                                    17
```

```
<210> SEQ ID NO 231
<211> LENGTH: 17
<212> TYPE: DNA
<213> ORGANISM: Triticum aestivum

<400> SEQUENCE: 231
ttggccgtgt aaggcag                                                    17

<210> SEQ ID NO 232
<211> LENGTH: 23
<212> TYPE: DNA
<213> ORGANISM: Triticum aestivum

<400> SEQUENCE: 232
tctcattcac acacaacact agc                                             23

<210> SEQ ID NO 233
<211> LENGTH: 21
<212> TYPE: DNA
<213> ORGANISM: Triticum aestivum

<400> SEQUENCE: 233
aatgaaaaaa cacttgcgtg g                                               21

<210> SEQ ID NO 234
<211> LENGTH: 20
<212> TYPE: DNA
<213> ORGANISM: Triticum aestivum

<400> SEQUENCE: 234
gcacattttt cactttcggg                                                 20

<210> SEQ ID NO 235
<211> LENGTH: 20
<212> TYPE: DNA
<213> ORGANISM: Triticum aestivum

<400> SEQUENCE: 235
atgacccttc tgccaaacac                                                 20

<210> SEQ ID NO 236
<211> LENGTH: 18
<212> TYPE: DNA
<213> ORGANISM: Triticum aestivum

<400> SEQUENCE: 236
atcgaccggg atctagcc                                                   18

<210> SEQ ID NO 237
<211> LENGTH: 19
<212> TYPE: DNA
<213> ORGANISM: Triticum aestivum

<400> SEQUENCE: 237
catccctacg ccactctgc                                                  19

<210> SEQ ID NO 238
<211> LENGTH: 21
<212> TYPE: DNA
<213> ORGANISM: Triticum aestivum

<400> SEQUENCE: 238
aatggtatct attccgaccc g                                               21
```

```
<210> SEQ ID NO 239
<211> LENGTH: 17
<212> TYPE: DNA
<213> ORGANISM: Triticum aestivum

<400> SEQUENCE: 239
tcaccgtggt caccgac                                                    17

<210> SEQ ID NO 240
<211> LENGTH: 20
<212> TYPE: DNA
<213> ORGANISM: Triticum aestivum

<400> SEQUENCE: 240
ccaccgagcc gataatgtac                                                 20

<210> SEQ ID NO 241
<211> LENGTH: 20
<212> TYPE: DNA
<213> ORGANISM: Triticum aestivum

<400> SEQUENCE: 241
tactggttca cattggtgcg                                                 20

<210> SEQ ID NO 242
<211> LENGTH: 19
<212> TYPE: DNA
<213> ORGANISM: Triticum aestivum

<400> SEQUENCE: 242
tcgccatcac tcgttcaag                                                  19

<210> SEQ ID NO 243
<211> LENGTH: 23
<212> TYPE: DNA
<213> ORGANISM: Triticum aestivum

<400> SEQUENCE: 243
ggattggagt taagagagaa ccg                                             23

<210> SEQ ID NO 244
<211> LENGTH: 20
<212> TYPE: DNA
<213> ORGANISM: Triticum aestivum

<400> SEQUENCE: 244
gcagagtgat caatgccaga                                                 20

<210> SEQ ID NO 245
<211> LENGTH: 20
<212> TYPE: DNA
<213> ORGANISM: Triticum aestivum

<400> SEQUENCE: 245
gtgaagcaga cccacaacac                                                 20

<210> SEQ ID NO 246
<211> LENGTH: 18
<212> TYPE: DNA
<213> ORGANISM: Triticum aestivum

<400> SEQUENCE: 246
gacggctgcg acgtagag                                                   18
```

<210> SEQ ID NO 247
<211> LENGTH: 21
<212> TYPE: DNA
<213> ORGANISM: Triticum aestivum

<400> SEQUENCE: 247
aattcaacct accaatctct g         21

<210> SEQ ID NO 248
<211> LENGTH: 21
<212> TYPE: DNA
<213> ORGANISM: Triticum aestivum

<400> SEQUENCE: 248
gcctaataaa ctgaaaacga g         21

<210> SEQ ID NO 249
<211> LENGTH: 21
<212> TYPE: DNA
<213> ORGANISM: Triticum aestivum

<400> SEQUENCE: 249
atcgtcacgt attttgcaat g         21

<210> SEQ ID NO 250
<211> LENGTH: 22
<212> TYPE: DNA
<213> ORGANISM: Triticum aestivum

<400> SEQUENCE: 250
tgcgtaagtc tagcattttc tg         22

<210> SEQ ID NO 251
<211> LENGTH: 19
<212> TYPE: DNA
<213> ORGANISM: Triticum aestivum

<400> SEQUENCE: 251
actacttagg cctcccgcc         19

<210> SEQ ID NO 252
<211> LENGTH: 20
<212> TYPE: DNA
<213> ORGANISM: Triticum aestivum

<400> SEQUENCE: 252
tgacccactt gcaattcatc         20

<210> SEQ ID NO 253
<211> LENGTH: 20
<212> TYPE: DNA
<213> ORGANISM: Triticum aestivum

<400> SEQUENCE: 253
gaggagtaag acacatgccc         20

<210> SEQ ID NO 254
<211> LENGTH: 20
<212> TYPE: DNA
<213> ORGANISM: Triticum aestivum

<400> SEQUENCE: 254

-continued

```
gtggctggag attcaggttc                                               20

<210> SEQ ID NO 255
<211> LENGTH: 21
<212> TYPE: DNA
<213> ORGANISM: Triticum aestivum

<400> SEQUENCE: 255
gcaagaagca acagcagtaa c                                             21

<210> SEQ ID NO 256
<211> LENGTH: 20
<212> TYPE: DNA
<213> ORGANISM: Triticum aestivum

<400> SEQUENCE: 256
cagatgctct tctctgctgg                                               20

<210> SEQ ID NO 257
<211> LENGTH: 20
<212> TYPE: DNA
<213> ORGANISM: Triticum aestivum

<400> SEQUENCE: 257
aggaaacaga aatatcgcgg                                               20

<210> SEQ ID NO 258
<211> LENGTH: 20
<212> TYPE: DNA
<213> ORGANISM: Triticum aestivum

<400> SEQUENCE: 258
aggactgtgg ggaatgaatg                                               20

<210> SEQ ID NO 259
<211> LENGTH: 18
<212> TYPE: DNA
<213> ORGANISM: Triticum aestivum

<400> SEQUENCE: 259
tcacgtggaa gacgctcc                                                 18

<210> SEQ ID NO 260
<211> LENGTH: 20
<212> TYPE: DNA
<213> ORGANISM: Triticum aestivum

<400> SEQUENCE: 260
ctacgtgcac caccattttg                                               20

<210> SEQ ID NO 261
<211> LENGTH: 20
<212> TYPE: DNA
<213> ORGANISM: Triticum aestivum

<400> SEQUENCE: 261
atcgcatgat gcacgtagag                                               20

<210> SEQ ID NO 262
<211> LENGTH: 21
<212> TYPE: DNA
<213> ORGANISM: Triticum aestivum

<400> SEQUENCE: 262
```
acatgcatgc ctacctaatg g                                        21

<210> SEQ ID NO 263
<211> LENGTH: 20
<212> TYPE: DNA
<213> ORGANISM: Triticum aestivum

<400> SEQUENCE: 263
ccgccctcat taagtttcac                                          20

<210> SEQ ID NO 264
<211> LENGTH: 22
<212> TYPE: DNA
<213> ORGANISM: Triticum aestivum

<400> SEQUENCE: 264
tttgacaagt acacgagtct gc                                       22

<210> SEQ ID NO 265
<211> LENGTH: 19
<212> TYPE: DNA
<213> ORGANISM: Triticum aestivum

<400> SEQUENCE: 265
aggagctcct ctgtgccac                                           19

<210> SEQ ID NO 266
<211> LENGTH: 19
<212> TYPE: DNA
<213> ORGANISM: Triticum aestivum

<400> SEQUENCE: 266
ttcgggactc tcttccctg                                           19

<210> SEQ ID NO 267
<211> LENGTH: 22
<212> TYPE: DNA
<213> ORGANISM: Triticum aestivum

<400> SEQUENCE: 267
catggacatt ttaccacaag ac                                       22

<210> SEQ ID NO 268
<211> LENGTH: 17
<212> TYPE: DNA
<213> ORGANISM: Triticum aestivum

<400> SEQUENCE: 268
tgcgtgtggt ccacctc                                             17

<210> SEQ ID NO 269
<211> LENGTH: 22
<212> TYPE: DNA
<213> ORGANISM: Triticum aestivum

<400> SEQUENCE: 269
ggttgctgta caagtgttca cg                                       22

<210> SEQ ID NO 270
<211> LENGTH: 20
<212> TYPE: DNA
<213> ORGANISM: Triticum aestivum -continued

```
<400> SEQUENCE: 270
cgggtgctgt gtgtaatgac                                              20

<210> SEQ ID NO 271
<211> LENGTH: 22
<212> TYPE: DNA
<213> ORGANISM: Triticum aestivum

<400> SEQUENCE: 271
cgagatacta tggaaggtga gg                                           22

<210> SEQ ID NO 272
<211> LENGTH: 19
<212> TYPE: DNA
<213> ORGANISM: Triticum aestivum

<400> SEQUENCE: 272
atctttgcaa ggattgccc                                               19

<210> SEQ ID NO 273
<211> LENGTH: 19
<212> TYPE: DNA
<213> ORGANISM: Triticum aestivum

<400> SEQUENCE: 273
caatgtggag acggtgtgc                                               19

<210> SEQ ID NO 274
<211> LENGTH: 18
<212> TYPE: DNA
<213> ORGANISM: Triticum aestivum

<400> SEQUENCE: 274
tgttgcatgc gatcatgc                                                18

<210> SEQ ID NO 275
<211> LENGTH: 22
<212> TYPE: DNA
<213> ORGANISM: Triticum aestivum

<400> SEQUENCE: 275
tcacaaaatg atttctcatc cg                                           22

<210> SEQ ID NO 276
<211> LENGTH: 19
<212> TYPE: DNA
<213> ORGANISM: Triticum aestivum

<400> SEQUENCE: 276
tgcagaaaac caacaaggg                                               19

<210> SEQ ID NO 277
<211> LENGTH: 22
<212> TYPE: DNA
<213> ORGANISM: Triticum aestivum

<400> SEQUENCE: 277
tttcttctgt cgttctcttc cc                                           22

<210> SEQ ID NO 278
<211> LENGTH: 19
<212> TYPE: DNA
<213> ORGANISM: Triticum aestivum
```

```
<400> SEQUENCE: 278
tttttacgcg tcaacgacg                                            19

<210> SEQ ID NO 279
<211> LENGTH: 20
<212> TYPE: DNA
<213> ORGANISM: Triticum aestivum

<400> SEQUENCE: 279
gcaatccacg agaagagagg                                           20

<210> SEQ ID NO 280
<211> LENGTH: 21
<212> TYPE: DNA
<213> ORGANISM: Triticum aestivum

<400> SEQUENCE: 280
cacaaactct tgacatgtgc g                                         21

<210> SEQ ID NO 281
<211> LENGTH: 20
<212> TYPE: DNA
<213> ORGANISM: Triticum aestivum

<400> SEQUENCE: 281
ttgctatcca tgtgccagag                                           20

<210> SEQ ID NO 282
<211> LENGTH: 21
<212> TYPE: DNA
<213> ORGANISM: Triticum aestivum

<400> SEQUENCE: 282
acatgtttca tgcaggtagc c                                         21

<210> SEQ ID NO 283
<211> LENGTH: 20
<212> TYPE: DNA
<213> ORGANISM: Triticum aestivum

<400> SEQUENCE: 283
agccagcaag tcaccaaaac                                           20

<210> SEQ ID NO 284
<211> LENGTH: 23
<212> TYPE: DNA
<213> ORGANISM: Triticum aestivum

<400> SEQUENCE: 284
agtgctggaa agagtagtga agc                                       23

<210> SEQ ID NO 285
<211> LENGTH: 18
<212> TYPE: DNA
<213> ORGANISM: Triticum aestivum

<400> SEQUENCE: 285
gcccggtcat gtaaaacg                                             18

<210> SEQ ID NO 286
<211> LENGTH: 22
<212> TYPE: DNA
```

<213> ORGANISM: Triticum aestivum

<400> SEQUENCE: 286
tttcagtttg cgttaagctt tg                22

<210> SEQ ID NO 287
<211> LENGTH: 20
<212> TYPE: DNA
<213> ORGANISM: Triticum aestivum

<400> SEQUENCE: 287
aatttcaaaa aggagagaga                20

<210> SEQ ID NO 288
<211> LENGTH: 20
<212> TYPE: DNA
<213> ORGANISM: Triticum aestivum

<400> SEQUENCE: 288
aacatgtgtt tttagctatc                20

<210> SEQ ID NO 289
<211> LENGTH: 19
<212> TYPE: DNA
<213> ORGANISM: Triticum aestivum

<400> SEQUENCE: 289
cgtactccac tccacacgg                19

<210> SEQ ID NO 290
<211> LENGTH: 20
<212> TYPE: DNA
<213> ORGANISM: Triticum aestivum

<400> SEQUENCE: 290
cggtccaagt gctacctttc                20

<210> SEQ ID NO 291
<211> LENGTH: 20
<212> TYPE: DNA
<213> ORGANISM: Triticum aestivum

<400> SEQUENCE: 291 cccttttaatc tcgctccctc                20

<210> SEQ ID NO 292
<211> LENGTH: 22
<212> TYPE: DNA
<213> ORGANISM: Triticum aestivum

<400> SEQUENCE: 292
gtctctttct cgtacttcca gg                22

<210> SEQ ID NO 293
<211> LENGTH: 21
<212> TYPE: DNA
<213> ORGANISM: Triticum aestivum

<400> SEQUENCE: 293
cctcttcctc cctcacttag c                21

<210> SEQ ID NO 294
<211> LENGTH: 18

```
<212> TYPE: DNA
<213> ORGANISM: Triticum aestivum

<400> SEQUENCE: 294
tgctaactgg cctttgcc                                                    18

<210> SEQ ID NO 295
<211> LENGTH: 20
<212> TYPE: DNA
<213> ORGANISM: Triticum aestivum

<400> SEQUENCE: 295
aattttcttc ctcacttatt                                                  20

<210> SEQ ID NO 296
<211> LENGTH: 20
<212> TYPE: DNA
<213> ORGANISM: Triticum aestivum

<400> SEQUENCE: 296
aaacgaacaa ccactcaatc                                                  20

<210> SEQ ID NO 297
<211> LENGTH: 21
<212> TYPE: DNA
<213> ORGANISM: Triticum aestivum

<400> SEQUENCE: 297
gcaatctttt ttctgaccac g                                                21

<210> SEQ ID NO 298
<211> LENGTH: 20
<212> TYPE: DNA
<213> ORGANISM: Triticum aestivum

<400> SEQUENCE: 298
acgaggcaag aacacacatg                                                  20

<210> SEQ ID NO 299
<211> LENGTH: 19
<212> TYPE: DNA
<213> ORGANISM: Triticum aestivum

<400> SEQUENCE: 299
ttcagtggta gcggtcgag                                                   19

<210> SEQ ID NO 300
<211> LENGTH: 20
<212> TYPE: DNA
<213> ORGANISM: Triticum aestivum

<400> SEQUENCE: 300
ccgacatctc atggatccac                                                  20

<210> SEQ ID NO 301
<211> LENGTH: 19
<212> TYPE: DNA
<213> ORGANISM: Triticum aestivum

<400> SEQUENCE: 301
tatccagagc agacggacg                                                   19

<210> SEQ ID NO 302
```

```
<211> LENGTH: 20
<212> TYPE: DNA
<213> ORGANISM: Triticum aestivum

<400> SEQUENCE: 302
ggtctagctt cgacgacacc                                              20

<210> SEQ ID NO 303
<211> LENGTH: 20
<212> TYPE: DNA
<213> ORGANISM: Triticum aestivum

<400> SEQUENCE: 303
caaggaaata ggcggtaact                                              20

<210> SEQ ID NO 304
<211> LENGTH: 20
<212> TYPE: DNA
<213> ORGANISM: Triticum aestivum

<400> SEQUENCE: 304
atttgagtct gaagtttgca                                              20

<210> SEQ ID NO 305
<211> LENGTH: 22
<212> TYPE: DNA
<213> ORGANISM: Triticum aestivum

<400> SEQUENCE: 305
caagcaaggt ttcgttttat cc                                           22

<210> SEQ ID NO 306
<211> LENGTH: 20
<212> TYPE: DNA
<213> ORGANISM: Triticum aestivum

<400> SEQUENCE: 306
gcatgtggtc catgtactgc                                              20

<210> SEQ ID NO 307
<211> LENGTH: 20
<212> TYPE: DNA
<213> ORGANISM: Triticum aestivum

<400> SEQUENCE: 307
ggcttccaga aaacaacagg                                              20

<210> SEQ ID NO 308
<211> LENGTH: 20
<212> TYPE: DNA
<213> ORGANISM: Triticum aestivum

<400> SEQUENCE: 308
atcggtgcgt accatcctac                                              20

<210> SEQ ID NO 309
<211> LENGTH: 21
<212> TYPE: DNA
<213> ORGANISM: Triticum aestivum

<400> SEQUENCE: 309
acctcatcca catgttctac g                                            21
```

-continued

```
<210> SEQ ID NO 310
<211> LENGTH: 17
<212> TYPE: DNA
<213> ORGANISM: Triticum aestivum

<400> SEQUENCE: 310
gcatggatag gacgccc                                                        17

<210> SEQ ID NO 311
<211> LENGTH: 21
<212> TYPE: DNA
<213> ORGANISM: Triticum aestivum

<400> SEQUENCE: 311
ccatgttgag taggttcagc c                                                   21

<210> SEQ ID NO 312
<211> LENGTH: 20
<212> TYPE: DNA
<213> ORGANISM: Triticum aestivum

<400> SEQUENCE: 312
cttggccaga agctacgaac                                                     20

<210> SEQ ID NO 313
<211> LENGTH: 21
<212> TYPE: DNA
<213> ORGANISM: Triticum aestivum

<400> SEQUENCE: 313
agcgttcttg ggaattagag a                                                   21

<210> SEQ ID NO 314
<211> LENGTH: 19
<212> TYPE: DNA
<213> ORGANISM: Triticum aestivum

<400> SEQUENCE: 314
ccaatcagcc tgcaacaac                                                      19

<210> SEQ ID NO 315
<211> LENGTH: 21
<212> TYPE: DNA
<213> ORGANISM: Triticum aestivum

<400> SEQUENCE: 315
tatggtcaaa gttggacctc g                                                   21

<210> SEQ ID NO 316
<211> LENGTH: 20
<212> TYPE: DNA
<213> ORGANISM: Triticum aestivum

<400> SEQUENCE: 316
aggctgcagc tcttcttcag                                                     20

<210> SEQ ID NO 317
<211> LENGTH: 20
<212> TYPE: DNA
<213> ORGANISM: Triticum aestivum

<400> SEQUENCE: 317
aaacagcgga tttcatcgag                                                     20
```

<210> SEQ ID NO 318
<211> LENGTH: 20
<212> TYPE: DNA
<213> ORGANISM: Triticum aestivum

<400> SEQUENCE: 318
tccgctgttg ttctgatctc                    20

<210> SEQ ID NO 319
<211> LENGTH: 21
<212> TYPE: DNA
<213> ORGANISM: Triticum aestivum

<400> SEQUENCE: 319
ctaattgcaa caggtcatgg g                  21

<210> SEQ ID NO 320
<211> LENGTH: 22
<212> TYPE: DNA
<213> ORGANISM: Triticum aestivum

<400> SEQUENCE: 320
tacttgtgtt ctgggacaat gg                 22

<210> SEQ ID NO 321
<211> LENGTH: 20
<212> TYPE: DNA
<213> ORGANISM: Triticum aestivum

<400> SEQUENCE: 321
gtaacttgtt gccaaagggg                    20

<210> SEQ ID NO 322
<211> LENGTH: 21
<212> TYPE: DNA
<213> ORGANISM: Triticum aestivum

<400> SEQUENCE: 322
acaaagtggc aaaaggagac a                  21

<210> SEQ ID NO 323
<211> LENGTH: 20
<212> TYPE: DNA
<213> ORGANISM: Triticum aestivum

<400> SEQUENCE: 323
ccatttcacc taatgcctgc                    20

<210> SEQ ID NO 324
<211> LENGTH: 23
<212> TYPE: DNA
<213> ORGANISM: Triticum aestivum

<400> SEQUENCE: 324
aataaaacca tgagctcact tgc                23

<210> SEQ ID NO 325
<211> LENGTH: 18
<212> TYPE: DNA
<213> ORGANISM: Triticum aestivum

<400> SEQUENCE: 325
ctgcaggcca tgatgatg                      18

<210> SEQ ID NO 326
<211> LENGTH: 18
<212> TYPE: DNA
<213> ORGANISM: Triticum aestivum

<400> SEQUENCE: 326
accgtgggtg ttgtgagc                          18

<210> SEQ ID NO 327
<211> LENGTH: 22
<212> TYPE: DNA
<213> ORGANISM: Triticum aestivum

<400> SEQUENCE: 327
gaccaagata ttcaaactgg cc                     22

<210> SEQ ID NO 328
<211> LENGTH: 20
<212> TYPE: DNA
<213> ORGANISM: Triticum aestivum

<400> SEQUENCE: 328
agctcagctt gcttggtacc                        20

<210> SEQ ID NO 329
<211> LENGTH: 20
<212> TYPE: DNA
<213> ORGANISM: Triticum aestivum

<400> SEQUENCE: 329
aatagagccc tgggactggg                        20

<210> SEQ ID NO 330
<211> LENGTH: 20
<212> TYPE: DNA
<213> ORGANISM: Triticum aestivum

<400> SEQUENCE: 330
gaaggacgac attccacctg                        20

<210> SEQ ID NO 331
<211> LENGTH: 22
<212> TYPE: DNA
<213> ORGANISM: Triticum aestivum

<400> SEQUENCE: 331
atagtgtgtt gcatgctgtg tg                     22

<210> SEQ ID NO 332
<211> LENGTH: 20
<212> TYPE: DNA
<213> ORGANISM: Triticum aestivum

<400> SEQUENCE: 332
tctaattagc gttggctgcc                        20

<210> SEQ ID NO 333
<211> LENGTH: 22
<212> TYPE: DNA
<213> ORGANISM: Triticum aestivum

<400> SEQUENCE: 333
attggcgact ctagcatata cg                                           22

<210> SEQ ID NO 334
<211> LENGTH: 22
<212> TYPE: DNA
<213> ORGANISM: Triticum aestivum

<400> SEQUENCE: 334
gggatgtctg ttccatctta gc                                           22

<210> SEQ ID NO 335
<211> LENGTH: 20
<212> TYPE: DNA
<213> ORGANISM: Triticum aestivum

<400> SEQUENCE: 335
gggctagaaa acaggaaggc                                              20

<210> SEQ ID NO 336
<211> LENGTH: 18
<212> TYPE: DNA
<213> ORGANISM: Triticum aestivum

<400> SEQUENCE: 336
tctcccggag ggtaggag                                                18

<210> SEQ ID NO 337
<211> LENGTH: 20
<212> TYPE: DNA
<213> ORGANISM: Triticum aestivum

<400> SEQUENCE: 337
gtcagataac gccgtccaat                                              20

<210> SEQ ID NO 338
<211> LENGTH: 20
<212> TYPE: DNA
<213> ORGANISM: Triticum aestivum

<400> SEQUENCE: 338
ctacgtgcac caccattttg                                              20

<210> SEQ ID NO 339
<211> LENGTH: 20
<212> TYPE: DNA
<213> ORGANISM: Triticum aestivum

<400> SEQUENCE: 339
acgccagttg atccgtaaac                                              20

<210> SEQ ID NO 340
<211> LENGTH: 21
<212> TYPE: DNA
<213> ORGANISM: Triticum aestivum

<400> SEQUENCE: 340
gacatcaata accgtggatg g                                            21

<210> SEQ ID NO 341
<211> LENGTH: 20
<212> TYPE: DNA
<213> ORGANISM: Triticum aestivum

<400> SEQUENCE: 341

-continued

```
ttttcattgt gccctctact                                          20

<210> SEQ ID NO 342
<211> LENGTH: 22
<212> TYPE: DNA
<213> ORGANISM: Triticum aestivum

<400> SEQUENCE: 342
gccaagtttc ttagctagtt aa                                       22

<210> SEQ ID NO 343
<211> LENGTH: 21
<212> TYPE: DNA
<213> ORGANISM: Triticum aestivum

<400> SEQUENCE: 343
ctacaattcg aaggagaggg g                                        21

<210> SEQ ID NO 344
<211> LENGTH: 21
<212> TYPE: DNA
<213> ORGANISM: Triticum aestivum

<400> SEQUENCE: 344
caccgcgtca actacttaag c                                        21

<210> SEQ ID NO 345
<211> LENGTH: 21
<212> TYPE: DNA
<213> ORGANISM: Triticum aestivum

<400> SEQUENCE: 345
atcatgtcga tctccttgac g                                        21

<210> SEQ ID NO 346
<211> LENGTH: 20
<212> TYPE: DNA
<213> ORGANISM: Triticum aestivum

<400> SEQUENCE: 346
tgccatgcac attagcagat                                          20

<210> SEQ ID NO 347
<211> LENGTH: 22
<212> TYPE: DNA
<213> ORGANISM: Triticum aestivum

<400> SEQUENCE: 347
aagtttcaca caagatctct cc                                       22

<210> SEQ ID NO 348
<211> LENGTH: 20
<212> TYPE: DNA
<213> ORGANISM: Triticum aestivum

<400> SEQUENCE: 348
tgacaagtac acgagtctgc                                          20

<210> SEQ ID NO 349
<211> LENGTH: 22
<212> TYPE: DNA
<213> ORGANISM: Triticum aestivum
```

-continued

<400> SEQUENCE: 349
atagcgaagt ctccctactc ca                                    22

<210> SEQ ID NO 350
<211> LENGTH: 17
<212> TYPE: DNA
<213> ORGANISM: Triticum aestivum

<400> SEQUENCE: 350
atgtgcatgt cggacgc                                          17

<210> SEQ ID NO 351
<211> LENGTH: 21
<212> TYPE: DNA
<213> ORGANISM: Triticum aestivum

<400> SEQUENCE: 351
tcatctgcta tttgtgctac a                                     21

<210> SEQ ID NO 352
<211> LENGTH: 19
<212> TYPE: DNA
<213> ORGANISM: Triticum aestivum

<400> SEQUENCE: 352
tcaaatacac caatgtgcc                                        19

<210> SEQ ID NO 353
<211> LENGTH: 20
<212> TYPE: DNA
<213> ORGANISM: Triticum aestivum

<400> SEQUENCE: 353
tacaaccgca agtaatgcca                                       20

<210> SEQ ID NO 354
<211> LENGTH: 20
<212> TYPE: DNA
<213> ORGANISM: Triticum aestivum

<400> SEQUENCE: 354
taccaacacc ctagcccttg                                       20

<210> SEQ ID NO 355
<211> LENGTH: 21
<212> TYPE: DNA
<213> ORGANISM: Triticum aestivum

<400> SEQUENCE: 355
tgtcatggat tatttggtcg g                                     21

<210> SEQ ID NO 356
<211> LENGTH: 21
<212> TYPE: DNA
<213> ORGANISM: Triticum aestivum

<400> SEQUENCE: 356
ctgcactctc ggtataccag c                                     21

<210> SEQ ID NO 357
<211> LENGTH: 17
<212> TYPE: DNA
<213> ORGANISM: Triticum aestivum

<400> SEQUENCE: 357
gtgctgccac cacttgc                                                    17

<210> SEQ ID NO 358
<211> LENGTH: 19
<212> TYPE: DNA
<213> ORGANISM: Triticum aestivum

<400> SEQUENCE: 358
tgtaggcact gcttgggag                                                  19

<210> SEQ ID NO 359
<211> LENGTH: 17
<212> TYPE: DNA
<213> ORGANISM: Triticum aestivum

<400> SEQUENCE: 359
cgacattggc ttcggtg                                                    17

<210> SEQ ID NO 360
<211> LENGTH: 20
<212> TYPE: DNA
<213> ORGANISM: Triticum aestivum

<400> SEQUENCE: 360
ataaaacagt gcggtccagg                                                 20

<210> SEQ ID NO 361
<211> LENGTH: 20
<212> TYPE: DNA
<213> ORGANISM: Triticum aestivum

<400> SEQUENCE: 361
tcgatttatt tgggccactg                                                 20

<210> SEQ ID NO 362
<211> LENGTH: 22
<212> TYPE: DNA
<213> ORGANISM: Triticum aestivum

<400> SEQUENCE: 362
gtataattcg ttcacagcac gc                                              22

<210> SEQ ID NO 363
<211> LENGTH: 18
<212> TYPE: DNA
<213> ORGANISM: Triticum aestivum

<400> SEQUENCE: 363
gcttgagacc ggcacagt                                                   18

<210> SEQ ID NO 364
<211> LENGTH: 20
<212> TYPE: DNA
<213> ORGANISM: Triticum aestivum

<400> SEQUENCE: 364
cgagaccttg agggtctaga                                                 20

<210> SEQ ID NO 365
<211> LENGTH: 21
<212> TYPE: DNA

-continued

<213> ORGANISM: Triticum aestivum

<400> SEQUENCE: 365
cccatacgat gatgtgtttc c    21

<210> SEQ ID NO 366
<211> LENGTH: 18
<212> TYPE: DNA
<213> ORGANISM: Triticum aestivum

<400> SEQUENCE: 366
caaacggaac atggtccc    18

<210> SEQ ID NO 367
<211> LENGTH: 22
<212> TYPE: DNA
<213> ORGANISM: Triticum aestivum

<400> SEQUENCE: 367
atcaacaagg tttgtgtgtt gg    22

<210> SEQ ID NO 368
<211> LENGTH: 17
<212> TYPE: DNA
<213> ORGANISM: Triticum aestivum

<400> SEQUENCE: 368
atgaaacgcg acctccc    17

<210> SEQ ID NO 369
<211> LENGTH: 21
<212> TYPE: DNA
<213> ORGANISM: Triticum aestivum

<400> SEQUENCE: 369
tgcttgtcta gattgcttgg g    21

<210> SEQ ID NO 370
<211> LENGTH: 19
<212> TYPE: DNA
<213> ORGANISM: Triticum aestivum

<400> SEQUENCE: 370
gatcgtctcg tccttggca    19

<210> SEQ ID NO 371
<211> LENGTH: 17
<212> TYPE: DNA
<213> ORGANISM: Triticum aestivum

<400> SEQUENCE: 371
gatctcccat gtccgcc    17

<210> SEQ ID NO 372
<211> LENGTH: 20
<212> TYPE: DNA
<213> ORGANISM: Triticum aestivum

<400> SEQUENCE: 372
cgacagtcgt cacttgccta    20

<210> SEQ ID NO 373
<211> LENGTH: 17

```
<212> TYPE: DNA
<213> ORGANISM: Triticum aestivum

<400> SEQUENCE: 373
gagcccacaa gctggca                                                        17

<210> SEQ ID NO 374
<211> LENGTH: 18
<212> TYPE: DNA
<213> ORGANISM: Triticum aestivum

<400> SEQUENCE: 374
tcgttctccc aaggcttg                                                       18

<210> SEQ ID NO 375
<211> LENGTH: 23
<212> TYPE: DNA
<213> ORGANISM: Triticum aestivum

<400> SEQUENCE: 375
aaacttagaa ctgtaatttc aga                                                 23

<210> SEQ ID NO 376
<211> LENGTH: 20
<212> TYPE: DNA
<213> ORGANISM: Triticum aestivum

<400> SEQUENCE: 376
agtgtgttca tttgacagtt                                                     20

<210> SEQ ID NO 377
<211> LENGTH: 17
<212> TYPE: DNA
<213> ORGANISM: Triticum aestivum

<400> SEQUENCE: 377
cgaggcagcg aggattt                                                        17

<210> SEQ ID NO 378
<211> LENGTH: 17
<212> TYPE: DNA
<213> ORGANISM: Triticum aestivum

<400> SEQUENCE: 378 tctccacta gccccgc                                                         17

<210> SEQ ID NO 379
<211> LENGTH: 21
<212> TYPE: DNA
<213> ORGANISM: Triticum aestivum

<400> SEQUENCE: 379
ttgtacatta agttcccatt a                                                   21

<210> SEQ ID NO 380
<211> LENGTH: 20
<212> TYPE: DNA
<213> ORGANISM: Triticum aestivum

<400> SEQUENCE: 380
tttaaggacc tacatgacac                                                     20

<210> SEQ ID NO 381
```

```
<211> LENGTH: 20
<212> TYPE: DNA
<213> ORGANISM: Triticum aestivum

<400> SEQUENCE: 381
atgagttccg ccaaagaatg                                              20

<210> SEQ ID NO 382
<211> LENGTH: 21
<212> TYPE: DNA
<213> ORGANISM: Triticum aestivum

<400> SEQUENCE: 382
acgaaataca caagtgggac a                                            21

<210> SEQ ID NO 383
<211> LENGTH: 22
<212> TYPE: DNA
<213> ORGANISM: Triticum aestivum

<400> SEQUENCE: 383
gatcaagact tttgtatctc tc                                           22

<210> SEQ ID NO 384
<211> LENGTH: 20
<212> TYPE: DNA
<213> ORGANISM: Triticum aestivum

<400> SEQUENCE: 384
gatgtccaac agttagctta                                              20

<210> SEQ ID NO 385
<211> LENGTH: 21
<212> TYPE: DNA
<213> ORGANISM: Triticum aestivum

<400> SEQUENCE: 385
cctatggtct ccatcatgag g                                            21

<210> SEQ ID NO 386
<211> LENGTH: 21
<212> TYPE: DNA
<213> ORGANISM: Triticum aestivum

<400> SEQUENCE: 386
tcatgtcaac tcaagaacac g                                            21

<210> SEQ ID NO 387
<211> LENGTH: 20
<212> TYPE: DNA
<213> ORGANISM: Triticum aestivum

<400> SEQUENCE: 387
gggtcttcat ccggaactct                                              20

<210> SEQ ID NO 388
<211> LENGTH: 21
<212> TYPE: DNA
<213> ORGANISM: Triticum aestivum

<400> SEQUENCE: 388
ccatgattta taaattccac c                                            21
```

```
<210> SEQ ID NO 389
<211> LENGTH: 21
<212> TYPE: DNA
<213> ORGANISM: Triticum aestivum

<400> SEQUENCE: 389
tttgttgggg gttaggatta g                                          21

<210> SEQ ID NO 390
<211> LENGTH: 22
<212> TYPE: DNA
<213> ORGANISM: Triticum aestivum

<400> SEQUENCE: 390
ccttaacact tgctggtagt ga                                         22

<210> SEQ ID NO 391
<211> LENGTH: 21
<212> TYPE: DNA
<213> ORGANISM: Triticum aestivum

<400> SEQUENCE: 391
aaaccatatt gggaggaaag g                                          21

<210> SEQ ID NO 392
<211> LENGTH: 20
<212> TYPE: DNA
<213> ORGANISM: Triticum aestivum

<400> SEQUENCE: 392
cacatggcat cacatttgtg                                            20

<210> SEQ ID NO 393
<211> LENGTH: 20
<212> TYPE: DNA
<213> ORGANISM: Triticum aestivum

<400> SEQUENCE: 393
attcggttcg ctagctacca                                            20

<210> SEQ ID NO 394
<211> LENGTH: 17
<212> TYPE: DNA
<213> ORGANISM: Triticum aestivum

<400> SEQUENCE: 394
acggagagca acctgcc                                               17

<210> SEQ ID NO 395
<211> LENGTH: 22
<212> TYPE: DNA
<213> ORGANISM: Triticum aestivum

<400> SEQUENCE: 395
tctgaacatt acacaaccct ga                                         22

<210> SEQ ID NO 396
<211> LENGTH: 21
<212> TYPE: DNA
<213> ORGANISM: Triticum aestivum

<400> SEQUENCE: 396
tgctctctct gaacctgaag c                                          21
```

-continued

<210> SEQ ID NO 397
<211> LENGTH: 22
<212> TYPE: DNA
<213> ORGANISM: Triticum aestivum

<400> SEQUENCE: 397
aatggcaatt ggaagacata gc                                           22

<210> SEQ ID NO 398
<211> LENGTH: 19
<212> TYPE: DNA
<213> ORGANISM: Triticum aestivum

<400> SEQUENCE: 398
ttcgcaatgt tgatttggc                                               19

<210> SEQ ID NO 399
<211> LENGTH: 21
<212> TYPE: DNA
<213> ORGANISM: Triticum aestivum

<400> SEQUENCE: 399
atggagtggt cacactttga a                                            21

<210> SEQ ID NO 400
<211> LENGTH: 22
<212> TYPE: DNA
<213> ORGANISM: Triticum aestivum

<400> SEQUENCE: 400
agcttctctg accaacttct cg                                           22

<210> SEQ ID NO 401
<211> LENGTH: 21
<212> TYPE: DNA
<213> ORGANISM: Triticum aestivum

<400> SEQUENCE: 401
caactcagtg ctcacacaac g                                            21

<210> SEQ ID NO 402
<211> LENGTH: 21
<212> TYPE: DNA
<213> ORGANISM: Triticum aestivum

<400> SEQUENCE: 402
cgataaccac tcatccacac c                                            21

<210> SEQ ID NO 403
<211> LENGTH: 17
<212> TYPE: DNA
<213> ORGANISM: Triticum aestivum

<400> SEQUENCE: 403
cggccctatc atggctg                                                 17

<210> SEQ ID NO 404
<211> LENGTH: 20
<212> TYPE: DNA
<213> ORGANISM: Triticum aestivum

<400> SEQUENCE: 404
gcttgcaagt tccattttgc                                              20

<210> SEQ ID NO 405
<211> LENGTH: 20
<212> TYPE: DNA
<213> ORGANISM: Triticum aestivum

<400> SEQUENCE: 405
tcatacgggt atggttggac                                          20

<210> SEQ ID NO 406
<211> LENGTH: 18
<212> TYPE: DNA
<213> ORGANISM: Triticum aestivum

<400> SEQUENCE: 406 caccccttg ttggtcac                                             18

<210> SEQ ID NO 407
<211> LENGTH: 22
<212> TYPE: DNA
<213> ORGANISM: Triticum aestivum

<400> SEQUENCE: 407
atgggttcgt actaacatca gc                                       22

<210> SEQ ID NO 408
<211> LENGTH: 20
<212> TYPE: DNA
<213> ORGANISM: Triticum aestivum

<400> SEQUENCE: 408
ttgctggtag cttcaatccc                                          20

<210> SEQ ID NO 409
<211> LENGTH: 22
<212> TYPE: DNA
<213> ORGANISM: Triticum aestivum

<400> SEQUENCE: 409
tgctgctact tgtacagagg ac                                       22

<210> SEQ ID NO 410
<211> LENGTH: 18
<212> TYPE: DNA
<213> ORGANISM: Triticum aestivum

<400> SEQUENCE: 410
ccgaattgtc cgccatag                                            18

<210> SEQ ID NO 411
<211> LENGTH: 20
<212> TYPE: DNA
<213> ORGANISM: Triticum aestivum

<400> SEQUENCE: 411
acatcgctct tcacaaaccc                                          20

<210> SEQ ID NO 412
<211> LENGTH: 19
<212> TYPE: DNA
<213> ORGANISM: Triticum aestivum

<400> SEQUENCE: 412

-continued agttccggtc atggctagg                    19

<210> SEQ ID NO 413
<211> LENGTH: 22
<212> TYPE: DNA
<213> ORGANISM: Triticum aestivum

<400> SEQUENCE: 413
attgaacagg aagacatcag gg                22

<210> SEQ ID NO 414
<211> LENGTH: 18
<212> TYPE: DNA
<213> ORGANISM: Triticum aestivum

<400> SEQUENCE: 414
ttcctggagc tgtctggc                     18

<210> SEQ ID NO 415
<211> LENGTH: 21
<212> TYPE: DNA
<213> ORGANISM: Triticum aestivum

<400> SEQUENCE: 415
gagagcctcg cgaaatatag g                 21

<210> SEQ ID NO 416
<211> LENGTH: 19
<212> TYPE: DNA
<213> ORGANISM: Triticum aestivum

<400> SEQUENCE: 416
tgcttctggt gttccttcg                    19

<210> SEQ ID NO 417
<211> LENGTH: 20
<212> TYPE: DNA
<213> ORGANISM: Triticum aestivum

<400> SEQUENCE: 417
gtagtgaaga caagggcatt                   20

<210> SEQ ID NO 418
<211> LENGTH: 20
<212> TYPE: DNA
<213> ORGANISM: Triticum aestivum

<400> SEQUENCE: 418
ccgaaagttg ggtgatatac                   20

<210> SEQ ID NO 419
<211> LENGTH: 22
<212> TYPE: DNA
<213> ORGANISM: Triticum aestivum

<400> SEQUENCE: 419
acttgtatgc tccattgatt gg                22

<210> SEQ ID NO 420
<211> LENGTH: 20
<212> TYPE: DNA
<213> ORGANISM: Triticum aestivum

<400> SEQUENCE: 420

```
ggggagtggaa aactgcataa                                              20

<210> SEQ ID NO 421
<211> LENGTH: 20
<212> TYPE: DNA
<213> ORGANISM: Triticum aestivum

<400> SEQUENCE: 421
ggctatctct ggcgctaaaa                                               20

<210> SEQ ID NO 422
<211> LENGTH: 19
<212> TYPE: DNA
<213> ORGANISM: Triticum aestivum

<400> SEQUENCE: 422
tccacaaaca agtagcgcc                                                19

<210> SEQ ID NO 423
<211> LENGTH: 20
<212> TYPE: DNA
<213> ORGANISM: Triticum aestivum

<400> SEQUENCE: 423
agccaccatc agcaaaaatt                                               20

<210> SEQ ID NO 424
<211> LENGTH: 20
<212> TYPE: DNA
<213> ORGANISM: Triticum aestivum

<400> SEQUENCE: 424
gaacatgagc agtttggcac                                               20

<210> SEQ ID NO 425
<211> LENGTH: 21
<212> TYPE: DNA
<213> ORGANISM: Triticum aestivum

<400> SEQUENCE: 425
atccgtagca cctactggtc a                                             21

<210> SEQ ID NO 426
<211> LENGTH: 20
<212> TYPE: DNA
<213> ORGANISM: Triticum aestivum

<400> SEQUENCE: 426
ggtctgttca tgccacattg                                               20

<210> SEQ ID NO 427
<211> LENGTH: 20
<212> TYPE: DNA
<213> ORGANISM: Triticum aestivum

<400> SEQUENCE: 427
aacacaatgg caaatgcaga                                               20

<210> SEQ ID NO 428
<211> LENGTH: 22
<212> TYPE: DNA
<213> ORGANISM: Triticum aestivum
```

-continued

```
<400> SEQUENCE: 428
ccttcctagt aagtgtgcct ca                                      22

<210> SEQ ID NO 429
<211> LENGTH: 20
<212> TYPE: DNA
<213> ORGANISM: Triticum aestivum

<400> SEQUENCE: 429
aatcacaaca aggcgtgaca                                         20

<210> SEQ ID NO 430
<211> LENGTH: 17
<212> TYPE: DNA
<213> ORGANISM: Triticum aestivum

<400> SEQUENCE: 430
cagggtggtg catgcat                                            17

<210> SEQ ID NO 431
<211> LENGTH: 19
<212> TYPE: DNA
<213> ORGANISM: Triticum aestivum

<400> SEQUENCE: 431
aaataggaca acccacggc                                          19

<210> SEQ ID NO 432
<211> LENGTH: 20
<212> TYPE: DNA
<213> ORGANISM: Triticum aestivum

<400> SEQUENCE: 432
tcaacttctt ggcctccatc                                         20

<210> SEQ ID NO 433
<211> LENGTH: 20
<212> TYPE: DNA
<213> ORGANISM: Triticum aestivum

<400> SEQUENCE: 433
actgcgtgtg cctacaattg                                         20

<210> SEQ ID NO 434
<211> LENGTH: 19
<212> TYPE: DNA
<213> ORGANISM: Triticum aestivum

<400> SEQUENCE: 434
tcactcgcac tcgataggc                                          19

<210> SEQ ID NO 435
<211> LENGTH: 20
<212> TYPE: DNA
<213> ORGANISM: Triticum aestivum

<400> SEQUENCE: 435
aaggcgaatc aaacggaata                                         20

<210> SEQ ID NO 436
<211> LENGTH: 20
<212> TYPE: DNA
<213> ORGANISM: Triticum aestivum
```

<400> SEQUENCE: 436
gttgctttag gggaaaagcc                                             20

<210> SEQ ID NO 437
<211> LENGTH: 21
<212> TYPE: DNA
<213> ORGANISM: Triticum aestivum

<400> SEQUENCE: 437
acataatgct tcctgtgcac c                                           21

<210> SEQ ID NO 438
<211> LENGTH: 20
<212> TYPE: DNA
<213> ORGANISM: Triticum aestivum

<400> SEQUENCE: 438 gccactttg tgtcgttcct                                              20

<210> SEQ ID NO 439
<211> LENGTH: 17
<212> TYPE: DNA
<213> ORGANISM: Triticum aestivum

<400> SEQUENCE: 439
gcatttcggg tgaaccc                                                17

<210> SEQ ID NO 440
<211> LENGTH: 22
<212> TYPE: DNA
<213> ORGANISM: Triticum aestivum

<400> SEQUENCE: 440
gttgcatgta tacgttaagc gg                                          22

<210> SEQ ID NO 441
<211> LENGTH: 22
<212> TYPE: DNA
<213> ORGANISM: Triticum aestivum

<400> SEQUENCE: 441
tctcgctgtg aaatcctatt tc                                          22

<210> SEQ ID NO 442
<211> LENGTH: 18
<212> TYPE: DNA
<213> ORGANISM: Triticum aestivum

<400> SEQUENCE: 442
aggcatggat agaggggc                                               18

<210> SEQ ID NO 443
<211> LENGTH: 22
<212> TYPE: DNA
<213> ORGANISM: Triticum aestivum

<400> SEQUENCE: 443
tagaattctt tatggggtct gc                                          22

<210> SEQ ID NO 444
<211> LENGTH: 22
<212> TYPE: DNA

-continued

<213> ORGANISM: Triticum aestivum

<400> SEQUENCE: 444
aggattccaa tccttcaaaa tt                                        22

<210> SEQ ID NO 445
<211> LENGTH: 20
<212> TYPE: DNA
<213> ORGANISM: Triticum aestivum

<400> SEQUENCE: 445
cccacaagaa cctttgaaga                                           20

<210> SEQ ID NO 446
<211> LENGTH: 19
<212> TYPE: DNA
<213> ORGANISM: Triticum aestivum

<400> SEQUENCE: 446
cattgtgtgt gcaaggcac                                            19

<210> SEQ ID NO 447
<211> LENGTH: 18
<212> TYPE: DNA
<213> ORGANISM: Triticum aestivum

<400> SEQUENCE: 447
tgcccacaac ggaacttg                                             18

<210> SEQ ID NO 448
<211> LENGTH: 20
<212> TYPE: DNA
<213> ORGANISM: Triticum aestivum

<400> SEQUENCE: 448
gcaaccacca agcacaaagt                                           20

<210> SEQ ID NO 449
<211> LENGTH: 22
<212> TYPE: DNA
<213> ORGANISM: Triticum aestivum

<400> SEQUENCE: 449
gcgtcagata tgcctaccta gg                                        22

<210> SEQ ID NO 450
<211> LENGTH: 20
<212> TYPE: DNA
<213> ORGANISM: Triticum aestivum

<400> SEQUENCE: 450
agtgagttag ccctgagcca                                           20

<210> SEQ ID NO 451
<211> LENGTH: 21
<212> TYPE: DNA
<213> ORGANISM: Triticum aestivum

<400> SEQUENCE: 451
tctgtctacc catgggattt g                                         21

<210> SEQ ID NO 452
<211> LENGTH: 20

```
<212> TYPE: DNA
<213> ORGANISM: Triticum aestivum

<400> SEQUENCE: 452
ctggcttcga ggtaagcaac                                              20

<210> SEQ ID NO 453
<211> LENGTH: 20
<212> TYPE: DNA
<213> ORGANISM: Triticum aestivum

<400> SEQUENCE: 453
ggaaacttat tgattgaaat                                              20

<210> SEQ ID NO 454
<211> LENGTH: 20
<212> TYPE: DNA
<213> ORGANISM: Triticum aestivum

<400> SEQUENCE: 454
tcaattttga cagaagaatt                                              20

<210> SEQ ID NO 455
<211> LENGTH: 18
<212> TYPE: DNA
<213> ORGANISM: Triticum aestivum

<400> SEQUENCE: 455
tcgcctttta cagtcggc                                                18

<210> SEQ ID NO 456
<211> LENGTH: 20
<212> TYPE: DNA
<213> ORGANISM: Triticum aestivum

<400> SEQUENCE: 456
atgggtagct gagagccaaa                                              20

<210> SEQ ID NO 457
<211> LENGTH: 20
<212> TYPE: DNA
<213> ORGANISM: Triticum aestivum

<400> SEQUENCE: 457
aagagataac atgcaagaaa                                              20

<210> SEQ ID NO 458
<211> LENGTH: 20
<212> TYPE: DNA
<213> ORGANISM: Triticum aestivum

<400> SEQUENCE: 458
ttcaaatatg tgggaactac                                              20

<210> SEQ ID NO 459
<211> LENGTH: 22
<212> TYPE: DNA
<213> ORGANISM: Triticum aestivum

<400> SEQUENCE: 459
atggcataat ttggtgaaat tg                                           22

<210> SEQ ID NO 460
```

```
<211> LENGTH: 22
<212> TYPE: DNA
<213> ORGANISM: Triticum aestivum

<400> SEQUENCE: 460
tgtttcaagc ccaacttcta tt                                              22

<210> SEQ ID NO 461
<211> LENGTH: 20
<212> TYPE: DNA
<213> ORGANISM: Triticum aestivum

<400> SEQUENCE: 461
aagcactacg aaaatatgac                                                 20

<210> SEQ ID NO 462
<211> LENGTH: 20
<212> TYPE: DNA
<213> ORGANISM: Triticum aestivum

<400> SEQUENCE: 462
tcttaagggg tgttatcata                                                 20

<210> SEQ ID NO 463
<211> LENGTH: 20
<212> TYPE: DNA
<213> ORGANISM: Triticum aestivum

<400> SEQUENCE: 463
ttcacaccca accaatagca                                                 20

<210> SEQ ID NO 464
<211> LENGTH: 20
<212> TYPE: DNA
<213> ORGANISM: Triticum aestivum

<400> SEQUENCE: 464
tctaggcaga cacatgcctg                                                 20

<210> SEQ ID NO 465
<211> LENGTH: 19
<212> TYPE: DNA
<213> ORGANISM: Triticum aestivum

<400> SEQUENCE: 465
gatccccaat tgcatgttg                                                  19

<210> SEQ ID NO 466
<211> LENGTH: 18
<212> TYPE: DNA
<213> ORGANISM: Triticum aestivum

<400> SEQUENCE: 466
cttgcaactg ggggacac                                                   18
```

MICROSATELLITE MARKERS FOR PLANTS OF THE SPECIES *TRITICUM AESTIVUM* AND *TRIBE TRITICEAE* AND THE USE OF SAID MARKERS

BACKGROUND OF THE INVENTION

The invention relates to novel genetic markers for wheats of the species Triticum aestivum and closely related species of the tribe Triticeae and to the use of said markers.

The most widely spread, known, DNA-based genetic markers are the so-called restriction fragment length polymorphisms (RFLP) markers. For using these markers, genomic DNA is digested with restriction enzymes, separated on agarose gels and transferred to nylon membranes (Southern Blot). Specific fragments are detected by hybridization with radioactively labeled DNA probes. When mutations occur in the region of the restriction enzymes used or when smaller deletions/insertions occur, polymorphisms between different lines are found, which are passed on stably and mostly codominantly. The use of RFLP markers in hexaploid cultivated wheat is possible only to a limited extent, since only very little polymorphism is detected in wheat in this manner.

It has already been described that microsatellite markers detect significantly more polymorphism between different wheat lines than do RFLP markers. This can be attributed particularly to the occurrence of multiple alleles per locus (Rbder et al., Mol. Gen. Genet. (1995) 246, 327–333). Moreover, it is known that microsatellite markers have the advantage that they can be detected by way of PCR and that therefore large amounts of samples can be analyzed more easily.

SUMMARY OF THE INVENTION

It is an object of the invention to provide novel microsatellite markers for the genetic analysis of plants of the *Triticum aestivum* species, which markers are distinguished by a degree of DNA polymorphism, which is higher than that of other molecular probes, that have been developed previously for the wheat genome.

This objective is accomplished as follows. The inventive markers are based on the amplification of certain hypervariable genome sections, the so-called microsatellites, with the help of their polymerase chain reaction (PCR). For specific amplification, two primers, in each to the case left and the right in the flanking sequences, are required for each microsatellite locus. On the average, these primers are 20 i 3 bases long and are defined by their sequences. In principle, a microsatellite marker is a sequence tagged site (STS), which is defined by two specific primers. These primers flank, in each case to the left and the right, a so-called microsatellite sequence. A microsatellite sequence is defined as a tandem repetitive repetition of a di-, tri- or tetranucleotide sequence, for example $(GA)_n$, in which n>10. Composite microsatellite sequences also occur, such as $(GT)_n (AT)_n$, as well as imperfect sequences, in which individual bases are mutated, such as $(GA)_n CA(GA)_n$. Among various lines and varieties, there is variation in the number of repeats at a certain locus. After amplification of the microsatellites, this leads, by means of the specific primers in the flanking sequences, to PCR products of different length and, with that, to polymorphisms. These polymorphisms are passed on stably and can therefore be used as genetic markers. In some cases, null alleles (no visible fragment) also occur, when there are mutations within the binding site for the primers.

The separation and detection of the PCR products obtained can be carried out with different technical variants. For separating the fragments, highly resolving agarose gels, native polyacrylamide gels or denaturing polyacrylamide gels (=sequencing gels) can be used. Depending on the separation system, fragments are detected using ethidium bromide staining, silver staining or, after labeling the PCR fragments radioactively, using autoradiography. A further, very effective variation for separation and detection consists of the use of an automatic sequencer with dye- or fluorescence-labeled primers. For this purpose, it is necessary to synthesize a dye- or fluorescence-labeled primer from each microsatellite primer pair. PCR amplification results in a labeled product, which can be detected by the sequencing equipment. At the same time, dye- or fluorescence-labeled size standards are also separated for each sample in the same track. After that, special software enable the absolute size of each fragment, which has been separated, to be calculated and, with that, also permits fragments from different gel runs to be compared. With this method, several hundred samples can be analyzed largely automatically in a day.

DETAILED DESCRIPTION OF THE INVENTION

Pursuant to the invention, microsatellite markers are made available, which contain the following primer pairs with assigned microsatellite sequences or a number thereof and amplify the loci of all chromosomes of the wheat genome and therefore find use for gene marking.

| WMS Number | WMS Primer Left | | WMS Primer Right | | Length (bp) in "cs" | Repeat Type | Annealing Temperature |
|---|---|---|---|---|---|---|---|
| WMS052 | 5' CTA TGA GGC GGA GGT TGA AG 3' | (SEQ. ID NO. 1) | 5' TGC GGT GCT CTT CCA TTT 3' | (SEQ. ID NO. 2) | 150 | GTimp | 60° C. |
| WMS055 | 5' GCA TCT GGT ACA CTA GCT GCC 3' | (SEQ. ID NO. 3) | 5' TCA TGG ATG CAT CAC ATC CT 3' | (SEQ. ID NO. 4) | 127 | GTimp | 60° C. |
| WMS057 | 5' TCG ATT CTG AAA GGT TCA TCG 3' | (SEQ. ID NO. 5) | 5' CGA TCA AGT TGC AGT TGA AGC CGC 3' | (SEQ. ID NO. 6) | 224 | AAAAAimp | 60° C. |
| WMS058 | 5' TCT GAT CCC GTG AGT GTA ACA 3' | (SEQ. ID NO. 7) | 5' GAA AAA AAT TGC ATA TGA GCC C 3' | (SEQ. ID NO. 8) | 118 | CA | 60° C. |
| WMS060 | 5' TGT CCT ACA CGG ACC ACG T3' | (SEQ. ID NO. 9) | 5' GCA TTG ACA GAT GCA CAC G 3' | (SEQ. ID NO. 10) | 211 | CA | 60° C. |
| WMS063 | 5' TCG ACC TGA TCG CCC CTA 3' | (SEQ. ID NO. 11) | 5' CGC CCT GGG TGA TAA TTT TGT TGG GT 3' | (SEQ. ID NO. 12) | 271 | GAA,CA,TA | 60° C. |
| WMS067 | 5' ACC ACA ACA AGA TCT GGG AAT G 3' | (SEQ. ID NO. 13) | 5' CAA CCC CCT AGA TGG GAG AAG CAC 3' | (SEQ. ID NO. 14) | 85 | CA | 60° C. |
| WMS068 | 5' AGG CCA GAA TCT GGG AGT GTC AT 3' | (SEQ. ID NO. 15) | 5' CTC CCT AGA TAC CGA GGA CAC 3' | (SEQ. ID NO. 16) | 182 | GA | 60° C. |
| WMS070 | 5' AGT GGC TGG GAG AGA CTC 3' | (SEQ. ID NO. 17) | 5' GCC CAT TAC GAG GTA CAC G 3' | (SEQ. ID NO. 18) | 194 | GT | 60° C. |
| WMS071 | 5' GGC AGA GTA GCG AGC ACC TG 3' | (SEQ. ID NO. 19) | 5' CAA GTG GAG CAT CCC GTG TTG 3' | (SEQ. ID NO. 20) | 128 | GT | 60° C. |
| WMS077 | 5' ACA TTA GAA GGT GCA ATG GG 3' | (SEQ. ID NO. 21) | 5' ACC CTC TTG ACC TGC ACC TTG 3' | (SEQ. ID NO. 22) | 153 | CA,GA | 55° C. |
| WMS082 | 5' ACG TAC AAC TAT GCG CTC GC 3' | (SEQ. ID NO. 23) | 5' AGT GGA TGC GTC ACC GAC TTT G 3' | (SEQ. ID NO. 24) | 152 | GT,GAimp | 60° C. |
| WMS088 | 5' CAC CAA ACA CAC CCT CC 3' | (SEQ. ID NO. 25) | 5' TCC ATT GGC TTC TCT CTC AA 3' | (SEQ. ID NO. 26) | 121 | GT | 60° C. |
| WMS095 | 5' GAT CAA ACA CAC ACC CCT CC 3' | (SEQ. ID NO. 27) | 5' AAT GCA AAG TGA AAA ACC CG 3' | (SEQ. ID NO. 28) | 121 | CA | 60° C. |
| WMS099 | 5' AAG ATG GAC GTA TGC ACA CA 3' | (SEQ. ID NO. 29) | 5' GCC ATA TTT GAT GAC GCA TA G 3' | (SEQ. ID NO. 30) | 119 | CA | 60° C. |
| WMS102 | 5' TCT CCC ATC CAA CGC CTC 3' | (SEQ. ID NO. 31) | 5' TGT TGG TGG CTT GAC TAT TG 3' | (SEQ. ID NO. 32) | 143 | CT | 60° C. |
| WMS106 | 5' CTG TTC CGT GGC ATT AA 3' | (SEQ. ID NO. 33) | 5' AAT AAG GAC ACA ATT GGG ATG G 3' | (SEQ. ID NO. 34) | 139 | GA | 60° C. |
| WMS107 | 5' ATT AAT ACC TGA GGG AGG TGC 3' | (SEQ. ID NO. 35) | 5' GGT CTC AGG AGC AGC AC 3' | (SEQ. ID NO. 36) | 195 | CT | 60° C. |
| WMS108 | 5' CAA CAA TGG GGT CCT AGC AT 3' | (SEQ. ID NO. 37) | 5' TGC ACA CTT AAA TTA CAT CCG C 3' | (SEQ. ID NO. 38) | 132 | GTimp | 60° C. |
| WMS111 | 5' TCT GTA GGC TCT CTC CGA CTG 3' | (SEQ. ID NO. 39) | 5' ACC TGA TCA GAT CCC ACT CG 3' | (SEQ. ID NO. 40) | 205 | CT,GT | 55° C. |
| WMS112 | 5' CTA AAC ACG ACA GCG GTG G 3' | (SEQ. ID NO. 41) | 5' GAT ATG GGT GCA ATA TG 3' | (SEQ. ID NO. 42) | 101 | CTimp | 55° C. |
| WMS113 | 5' ATT CGA GGT TAG GAG GAG G 3' | (SEQ. ID NO. 43) | 5' GAG GGT GGG CCT ATA AGA CC 3' | (SEQ. ID NO. 44) | 148 | GT | 60° C. |
| WMS114 | 5' ACA AAC AGA AAA TCA AAA CCC G 3' | (SEQ. ID NO. 45) | 5' ATC CAT CGC CAT TGG AGT 3' | (SEQ. ID NO. 46) | 206 (177) | GA | 60° C. |
| WMS118 | 5' GAT GTT GCC ACT TGA GCA TG 3' | (SEQ. ID NO. 47) | 5' GAT TAG TCA AAT GGA ACA CCC C 3' | (SEQ. ID NO. 48) | 110 | CA | 60° C. |
| WMS119 | 5' TGA CTA ACA TCC TTT GTC ACG C 3' | (SEQ. ID NO. 49) | 5' CAT GTC TCA ACC ACC CAC AG 3' | (SEQ. ID NO. 50) | 181 | GTimp | 55° C. |
| WMS120 | 5' AAT CCC CAC CGA TTC TTC TC 3' | (SEQ. ID NO. 51) | 5' GAT TAT ACT GGT ACC GTA AC 3' | (SEQ. ID NO. 52) | 139 | CT,CA | 55° C. |
| WMS121 | 5' TCC TCT ACA AAC ACA GAT G 3' | (SEQ. ID NO. 53) | 5' CTC GCA ACT AGA AGT TTC CTG G 3' | (SEQ. ID NO. 54) | 143 | CA | 50° C. |
| WMS122 | 5' GGG TGG GAG CTT AAA GGA T 3' | (SEQ. ID NO. 55) | 5' AAA ACC ATC CTC CAT CCG AG 3' | (SEQ. ID NO. 56) | 149 | CT,CA | 60° C. |
| WMS124 | 5' GCC ATG GCT AGG ACC CAG 3' | (SEQ. ID NO. 57) | 5' ACT GTT CGG TGC AAT TTG AG 3' | (SEQ. ID NO. 58) | 213 | CA,GTimp | 60° C. |
| WMS126 | 5' CAT ACG CTC CAC CAT GAC 3' | (SEQ. ID NO. 59) | 5' GTT GAG ATG ATG GAG G 3' | (SEQ. ID NO. 60) | 196 | CA | 60° C. |
| WMS128 | 5' AGC ACA TTT TAA CAC AGA TA 3' | (SEQ. ID NO. 61) | 5' ATC CTG TGA ATT TTG AAA AC 3' | (SEQ. ID NO. 62) | 176 | CA | 50° C. |
| WMS129 | 5' TCA GTG GCT AAG CTA CAC AG 3' | (SEQ. ID NO. 63) | 5' AAA ACT TAG TAG CCG CGT 3' | (SEQ. ID NO. 64) | 221 | GTimp | 55° C. |
| WMS130 | 5' AGC TCT GCT TCA CGA GGA AG 3' | (SEQ. ID NO. 65) | 5' CTC CTC TTT ATA TCG CGT CCC 3' | (SEQ. ID NO. 66) | 113 | CA | 60° C. |
| WMS131 | 5' AAT CCC CAC CGA TTC TTC TC 3' | (SEQ. ID NO. 67) | 5' AGT TCC TGG GTC CTT GAT GG 3' | (SEQ. ID NO. 68) | 131 | CT | 55° C. |
| WMS132 | 5' TAC TCT ACA ATC ACA CGG T G 3' | (SEQ. ID NO. 69) | 5' CAT ATC AAG GTC TCC TTC CCC 3' | (SEQ. ID NO. 70) | 119 | GA,GAA | 60° C. |
| WMS133 | 5' ATC TAA ACA AGA CGG CGG TG 3' | (SEQ. ID NO. 71) | 5' CAA AGC AAT TGT GAC AAC AAA G 3' | (SEQ. ID NO. 72) | 118 | CT | 60° C. |
| WMS134 | 5' CAT GGA ACT AGG ACC CAG 3' | (SEQ. ID NO. 73) | 5' ACT GTT CGG TGC AAT TTG AGG 3' | (SEQ. ID NO. 74) | 111 | CA | 60° C. |
| WMS135 | 5' TGT CAA CGT CTT GAA AAG 3' | (SEQ. ID NO. 75) | 5' ACA CTG ACC CAA ACC TG 3' | (SEQ. ID NO. 76) | 143 | GA | 55° C. |
| WMS136 | 5' GAC ACC ACC TTC CCC TTT G 3' | (SEQ. ID NO. 77) | 5' CAT CGG CAA GGT GCT AT C 3' | (SEQ. ID NO. 78) | 62 | CT | 60° C. |
| WMS140 | 5' ATG GAG ATA TTT GGC CTA CAA C 3' | (SEQ. ID NO. 79) | 5' CTT GAC TTC AAG GCG TGA CA 3' | (SEQ. ID NO. 80) | 296 | CT | 50° C. |
| WMS144 | 5' TTT GCT GTG GTA CGA AAC ATA C 3' | (SEQ. ID NO. 81) | 5' ACT CTC TAA TGT CTA ATA AAA C 3' | (SEQ. ID NO. 82) | 251 | CT | 60° C. |
| WMS146 | 5' CCA AAA CTG AAA CTG TC 3' | (SEQ. ID NO. 83) | 5' CTC CTG CAT TGG TCC TTG G 3' | (SEQ. ID NO. 84) | 200 | GT | 60° C. |
| WMS148 | 5' GTG AAG CAG CAA CTG GAG AA 3' | (SEQ. ID NO. 85) | 5' CAA AGC ACT AGG ACC AAA C 3' | (SEQ. ID NO. 86) | 163 | CA | 55° C. |
| WMS149 | 5' CAT TGT TTT CTG CCT CTA GCC 3' | (SEQ. ID NO. 87) | 5' CTA GCA TCG AAC CTG AAC AAG 3' | (SEQ. ID NO. 88) | 161 | GAimp | 60° C. |
| WMS153 | 5' GAT CTC GTC ACC GAG AAT TC 3' | (SEQ. ID NO. 89) | 5' TGG TAG AGA TGT CTG CA 3' | (SEQ. ID NO. 90) | 188 | GA | 60° C. |
| WMS154 | 5' TCA CAG AGA GAG GGA AA 3' | (SEQ. ID NO. 91) | 5' ATG CAT TGT ACA TGC TGC CA 3' | (SEQ. ID NO. 92) | 102 | GA | 55° C. |
| WMS155 | 5' CAA TCA TTT CCC CCT CCC 3' | (SEQ. ID NO. 93) | 5' AAT CAT TGT AAA TCC AGT GC C 3' | (SEQ. ID NO. 94) | 141 | CT | 60° C. |

-continued

| WMS Number | WMS Primer Left | WMS Primer Right | Length (bp) in "cs" | Repeat Type | Annealing Temperature |
|---|---|---|---|---|---|
| WMS156 | 5' CCA ACC GTG CTA TTA GTC ATT C 3' (SEQ. ID NO. 95) | 5' CAA TGC AGG CCC TCC TAA C 3' (SEQ. ID NO. 96) | 277 | GT | 60° C. |
| WMS157 | 5' GTC GTC GCG GTA AGC TTG 3' (SEQ. ID NO. 97) | 5' GAG TGA GCT CAC GAG GCT TG 3' (SEQ. ID NO. 98) | 106 | CT | 60° C. |
| WMS159 | 5' GGG CCA CTG GAA CAC 3' (SEQ. ID NO. 99) | 5' GCA GAA GCT TGT TAG GC 3' (SEQ. ID NO. 100) | 192 | GT | 60° C. |
| WMS160 | 5' TTC AAT TCA GTC TTG GCT TGG 3' (SEQ. ID NO. 101) | 5' CTG CAG GAA AAA TAC ACC C 3' (SEQ. ID NO. 102) | 184 | GA | 60° C. |
| WMS161 | 5' GAT CGA GTG ATG GCA GAT GG 3' (SEQ. ID NO. 103) | 5' TGT GAA TTA CTT GGA CGT GG 3' (SEQ. ID NO. 104) | 154 | CT | 60° C. |
| WMS162 | 5' AGT GGA TCG ACA AGG CTC TG 3' (SEQ. ID NO. 105) | 5' AGA AGA AGC AAA CGA TTC CC 3' (SEQ. ID NO. 106) | 208 | CA | 60° C. |
| WMS163 | 5' ACC TCG ACA GAC CTG GTA CG 3' (SEQ. ID NO. 107) | 5' GTC TTT GTC TAA ACA AAT CGC AC 3' (SEQ. ID NO. 108) | 127 | CT | 55° C. |
| WMS164 | 5' ACA TTT CTC CCC CAT CGT C 3' (SEQ. ID NO. 109) | 5' TTG TAA ACA AAT CGC ATG CG 3' (SEQ. ID NO. 110) | 120 | CT | 55° C. |
| WMS165 | 5' TGC AGT GGT CAG ATG TTT CC 3' (SEQ. ID NO. 111) | 5' CTT TTC TTT CAG ATT GCG CC 3' (SEQ. ID NO. 112) | 199 | GA | 60° C. |
| WMS169 | 5' ACC ACT GCA GAG AAC ACA TAC G 3' (SEQ. ID NO. 113) | 5' GTG CTC TGC TCT AAG TGT GGG 3' (SEQ. ID NO. 114) | 196 | GA | 60° C. |
| WMS174 | 5' CCG TTC CTA TCT GTT AAA TCC C 3' (SEQ. ID NO. 115) | 5' GAC ACA CAT GTT GCC AC 3' (SEQ. ID NO. 116) | 173 | CT | 55° C. |
| WMS179 | 5' AAG TTG AGT TGA TGC GGG AG 3' (SEQ. ID NO. 117) | 5' CCA TGA CCA GCA TCC ACT C 3' (SEQ. ID NO. 118) | 181 | GT | 55° C. |
| WMS180 | 5' ATC CGC GTA AGG AAT AGT GT 3' (SEQ. ID NO. 119) | 5' GAT CGC ACG GGA AGA G 3' (SEQ. ID NO. 120) | 84 | CT | 50° C. |
| WMS181 | 5' TCA TTG GTA ATG AGG AGA GA 3' (SEQ. ID NO. 121) | 5' GAA CTC CAC ATG TGC ATG TC 3' (SEQ. ID NO. 122) | 135 | GA | 50° C. |
| WMS182 | 5' TGA TGT AGT GGA CCC ATA GGC 3' (SEQ. ID NO. 123) | 5' TTG CAC GCC AAA TAA CA 3' (SEQ. ID NO. 124) | 165 | CT | 50° C. |
| WMS186 | 5' GCA GAG CCT GGT TCA AAA AG 3' (SEQ. ID NO. 125) | 5' CGC CTC TAG CGA GAG CTA TG 5' (SEQ. ID NO. 126) | 140 | GA | 60° C. |
| WMS189 | 5' AGG AGC AGC GGA ACG AAC 3' (SEQ. ID NO. 127) | 5' AGA AAT ACG GAA ACC CAC AA 3' (SEQ. ID NO. 128) | 117 | CA | 60° C. |
| WMS190 | 5' GTG CTT GCT GAG CTA TGA GTC 3' (SEQ. ID NO. 129) | 5' GTG CCA CGT ACG ACC TTT G 3' (SEQ. ID NO. 130) | >201 | CT,GT | 60° C. |
| WMS191 | 5' AGA CTG TTT CTT TCA GAT TGC GC 3' (SEQ. ID NO. 131) | 5' TAG CAC AGT TGT ATG CAT G 3' (SEQ. ID NO. 132) | 128 | CT | 60° C. |
| WMS192 | 5' GGT TTT TGT GCA CCT TAC TCC 3' (SEQ. ID NO. 133) | 5' CGT TGT CTA ATC TTG CCT TGC 3' (SEQ. ID NO. 134) | 191 | CT | 60° C. |
| WMS193 | 5' CTT TGT GCA CCT TAC TCT CC 3' (SEQ. ID NO. 135) | 5' AAT TGT GTT GAT GAT TTG GGG 3' (SEQ. ID NO. 136) | 171 | CT,CA | 60° C. |
| WMS194 | 5' GAT CTG CGT CTC TAC AG 3' (SEQ. ID NO. 137) | 5' CGA CGC AGA ACT TAA ACA AG 3' (SEQ. ID NO. 138) | 131 | CT | 50° C. |
| WMS195 | 5' GAG TGC CGT GGT GTC TAC 3' (SEQ. ID NO. 139) | 5' ACC CCC AAT GCA GTC AGA GAG 3' (SEQ. ID NO. 140) | 108 | CT | 60° C. |
| WMS197 | 5' GAG AAA GAG GTC TGG AGG TCG 3' (SEQ. ID NO. 141) | 5' CCA AAT GCA TGG GCA CAT GTG 3' (SEQ. ID NO. 142) | 126 | CT | 60° C. |
| WMS198 | 5' TTG AAC CGG AAG TAC AGC AG 3' (SEQ. ID NO. 143) | 5' TCA GTT TAT TTT AGA GCA AGC G 3' (SEQ. ID NO. 144) | 130 | CA | 60° C. |
| WMS200 | 5' TCA ACG GAA CAG GCG CAA G 3' (SEQ. ID NO. 145) | 5' GAC CTG ATG ATG AGA GCA AC 3' (SEQ. ID NO. 146) | 250 | CA,GA | 60° C. |
| WMS203 | 5' CCC AAA GCA GCA GCG CAA GC 3' (SEQ. ID NO. 147) | 5' ACC AAT GCT GTT ATC GTG TCG 3' (SEQ. ID NO. 148) | 139 | CT | 60° C. |
| WMS205 | 5' CGA CCC CGT TCA CTT CAG 3' (SEQ. ID NO. 149) | 5' AGT CGC CGT GTT ATA GCC 3' (SEQ. ID NO. 150) | 152 | GA | 60° C. |
| WMS210 | 5' TGC ATC AAG AAT TTG AGT GTG CAA G 3' (SEQ. ID NO. 151) | 5' TGA GAG GAA CTT GTT GAA AGG A 3' (SEQ. ID NO. 152) | 192 | GA | 50° C. |
| WMS212 | 5' AAG CAA CAT CAT GTC CTG CAA TG 3' (SEQ. ID NO. 153) | 5' TGC AGT AGT CCA TCT CGT TC 3' (SEQ. ID NO. 154) | 104 | CT | 60° C. |
| WMS213 | 5' CCC CTG GCT CGT TCT ATC TC 3' (SEQ. ID NO. 155) | 5' CTA GCT TAG CAC TGC AC 3' (SEQ. ID NO. 156) | 184 | GA | 55° C. |
| WMS218 | 5' CGG GAA CAC GGA GCA CAC 3' (SEQ. ID NO. 157) | 5' AAC AGT AAC AGT TGC CGC AGC C 3' (SEQ. ID NO. 158) | 149 | CT | 60° C. |
| WMS219 | 5' GAT GAG CAG CAC CAC TGC 3' (SEQ. ID NO. 159) | 5' GGG GTC CGA GTC CAC AAC 3' (SEQ. ID NO. 160) | 181 | GAimp | 60° C. |
| WMS224 | 5' TGA GTC CAG CCT TGC TGC 3' (SEQ. ID NO. 161) | 5' CAA CAT CCG CTA TTC AA 3' (SEQ. ID NO. 162) | 142 | CT | 50° C. |
| WMS228 | 5' TCA TAT TGA CCT CTT CCC TAG G 3' (SEQ. ID NO. 163) | 5' GTG CCG CCG CTT CGT C 3' (SEQ. ID NO. 164) | 210 | CT,CA | 55° C. |
| WMS231 | 5' AGC TCG GGA TGA GCA GTG 3' (SEQ. ID NO. 165) | 5' GAT CCG CCG CTT TTT 3' (SEQ. ID NO. 166) | 130 | GAimp | 55° C. |
| WMS232 | 5' ATC TCA ACG CCA GCA CG 3' (SEQ. ID NO. 167) | 5' TGA GAG TTG GAA GGC TCA CAC CT 3' (SEQ. ID NO. 168) | 141 | GA | 55° C. |
| WMS233 | 5' TCA AAA CAT AAA TGT TCA TTG GA 3' (SEQ. ID NO. 169) | 5' TCA ACC GTG TGT ATT TTT GTC C 3' (SEQ. ID NO. 170) | 261 | CT | 55° C. |
| WMS234 | 5' GAG TCC TGA TGT GAA GCT GTT G 3' (SEQ. ID NO. 171) | 5' CTC CAT TGC GAA CAT CCA TG 3' (SEQ. ID NO. 172) | 241 | CT,CA | 60° C. |
| WMS237 | 5' GAA TCA GTG TCA AGG CAT CTG 3' (SEQ. ID NO. 173) | 5' CTG AGT GCA TGC CAT GCA AC 3' (SEQ. ID NO. 174) | 137 | CT | 55° C. |
| WMS238 | 5' CGG CTT CTA CCG CTC ACC 3' (SEQ. ID NO. 175) | 5' AGT GCC TTG CCG AGG TC 3' (SEQ. ID NO. 176) | 204 | CT,GT,GGGT | 55° C. |
| WMS241 | 5' TCT TCC AAC TAA AGC ATA GC 3' (SEQ. ID NO. 177) | 5' CTT CCA TGG ACT ACA TAG C 3' (SEQ. ID NO. 178) | 146 | GA | 55° C. |
| WMS242 | 5' GGC AGC TGG AGC AGG 3' (SEQ. ID NO. 179) | 5' TGT TGG CAT TTC CTA TGC AT 3' (SEQ. ID NO. 180) | 142 | GA | 55° C. |
| WMS244 | 5' CAG CGC AGC GAT TAG GC 3' (SEQ. ID NO. 181) | 5' TTT ATC TGT TCA TTC GAG CGC 3' (SEQ. ID NO. 182) | 227 | GAimp | 60° C. |
| WMS245 | 5' GCA ATC TTT TTT CTG ACC ACG 3' (SEQ. ID NO. 183) | 5' ATG TGC ATG TTC TCG GAC GC 3' (SEQ. ID NO. 184) | 141 | CT | 60° C. |
| WMS247 | 5' AGG ACT TCC GCA CCC ACG 3' (SEQ. ID NO. 185) | 5' TGG CCT GGT CTT CCT CTA GC 3' (SEQ. ID NO. 186) | 158 | GA | 60° C. |
| WMS248 | 5' AAG ATG GAT CGA GAA AGG GA 3' (SEQ. ID NO. 187) | 5' ATC TGT TCC TTC GAG TAC c 3' (SEQ. ID NO. 188) | 185 | CA | 60° C. |
| WMS249 | 5' ACA CTG CTC ACG AGT CTG GC 3' (SEQ. ID NO. 189) | 5' CTG CCG CCA TTT GTT C 3' (SEQ. ID NO. 190) | 177 | GAimp | 60° C. |
| WMS251 | 5' CAA CTG GTT GCT ACA CAA GA 3' (SEQ. ID NO. 191) | 5' GGG ATG TGT TGT CCA TCT TAG 3' (SEQ. ID NO. 192) | 103 | CA | 55° C. |

-continued

| WMS Number | WMS Primer Left | WMS Primer Right | Length (bp) in "cs" | Repeat Type | Annealing Temperature |
|---|---|---|---|---|---|
| WMS255 | 5' CAA CTG TAC GGT TTC ATT GC 3' (SEQ. ID NO. 193) | 5' TCT GCC GTA AGT CGC CTC 3' (SEQ. ID NO. 194) | 148 | GA | 55° C. |
| WMS257 | 5' AGA GTG CAT GGT TCT GGG ACG 3' (SEQ. ID NO. 195) | 5' CCA AGA CGA TGC TGA AGT CA 3' (SEQ. ID NO. 196) | 192 | GT | 60° C. |
| WMS258 | 5' GAT CGC TTC ATC TCT TCT C 3' (SEQ. ID NO. 197) | 5' GTA CAC GCC GTA GGC CC 3' (SEQ. ID NO. 198) | >81 | CT | 60° C. |
| WMS259 | 5' AGG GAA AAG ACA TCT TTT TC 3' (SEQ. ID NO. 199) | 5' CGA CCG ACT TCG GGT TC 3' (SEQ. ID NO. 200) | 105 | GA | 55° C. |
| WMS260 | 5' GCC CCT TGA CGC CTA AGG C 3' (SEQ. ID NO. 201) | 5' CGC GCG TAC AGG CC3' (SEQ. ID NO. 202) | 157 | GA | 55° C. |
| WMS261 | 5' CTC CCT GTA CGC CTA AGG C 3' (SEQ. ID NO. 203) | 5' CTC GCG TTC ATT GCC ATT g 3' (SEQ. ID NO. 204) | 192 | CT | 55° C. |
| WMS263 | 5' TCT GCC GTA AGT GCT TCT 3' (SEQ. ID NO. 205) | 5' GGT TTC ATT TGC CCT AA 3' (SEQ. ID NO. 206) | 134 | CT | 55° C. |
| WMS264 | 5' GAG AAA CAT GCC GAA CAA CA 3' (SEQ. ID NO. 207) | 5' GCA TGC ATG AGA ATA GGA ACT 3' (SEQ. ID NO. 208) | 219 | CA | 60° C. |
| WMS265 | 5' TGT TGC GGA TGG TCA CTA TT 3' (SEQ. ID NO. 209) | 5' GAG TAC ACA TTT GGC CTC TGC 3' (SEQ. ID NO. 210) | 200 | GT | 55° C. |
| WMS268 | 5' AGG GGA TAA TAA GTT GTC ACT CCA 3' (SEQ. ID NO. 211) | 5' TTA TGT TGC GTA CGT ACC CA 3' (SEQ. ID NO. 212) | 241 | GAimp | 55° C. |
| WMS269 | 5' TGC ATA TAA ACA ACA CAC CC 3' (SEQ. ID NO. 213) | 5' TTT GAG CTC CAA AGT AGA TTA Gc 3' (SEQ. ID NO. 214) | >148 | CA | 60° C. |
| WMS271 | 5' CAA GAT CGT GGA GCC AGC 3' (SEQ. ID NO. 215) | 5' AGC TGC TAG CTT TTG GGA CA 3' (SEQ. ID NO. 216) | 162 | CT, GA | 60° C. |
| WMS272 | 5' TGC TCT TTG GCG AAT ATA TGG 3' (SEQ. ID NO. 217) | 5' GTT CAA AAC AAA TTA GGC AAA cc 3' (SEQ. ID NO. 218) | 140 | CA | 55° C. |
| WMS273 | 5' ATT GGA CAA ACA GAT GCT TT 3' (SEQ. ID NO. 219) | 5' AGC AGT GAA GAG GAA GAT C 3' (SEQ. ID NO. 220) | 167 | GA | 55° C. |
| WMS274 | 5' AAC TTG CAA ACA TGT TCT GA 3' (SEQ. ID NO. 221) | 5' TAT TTG AAG CAG TGT AAA TT 3' (SEQ. ID NO. 222) | 179 | GT | 50° C. |
| WMS275 | 5' AAT TTT CTT CAC TTA TTC T 3' (SEQ. ID NO. 223) | 5' AAC AAA AAA TTA GGG CC 3' (SEQ. ID NO. 224) | 107 | CT | 50° C. |
| WMS276 | 5' ATT TGC CTG AAG AAA ATA TT 3' (SEQ. ID NO. 225) | 5' AAT TTC ACT GCA TAC ACA AG 3' (SEQ. ID NO. 226) | 99 | CT | 55° C. |
| WMS278 | 5' GTT GCT TCA TGA ACG CTC AA 3' (SEQ. ID NO. 227) | 5' CTG CCC AAT TTT CAC TC 3' (SEQ. ID NO. 228) | 241 | GTimpGAimp | 55° C. |
| WMS281 | 5' CGG CCA TAT TTC TGT AAG TAT GC 3' (SEQ. ID NO. 229) | 5' GCA GGT AAT GGC CGG AC 3' (SEQ. ID NO. 230) | 135 | GT | 60° C. |
| WMS282 | 5' TTG GCC GTG TAA GGT AG 3' (SEQ. ID NO. 231) | 5' TCT CAT TCA ACA ACA CTA GC 3' (SEQ. ID NO. 232) | 220 | GA | 55° C. |
| WMS284 | 5' AAT GAA AAA ACA CTT GCG TGG 3' (SEQ. ID NO. 233) | 5' GCA CAT TTT TCA CTT TCG GG 3' (SEQ. ID NO. 234) | 123 | GA | 60° C. |
| WMS285 | 5' ATG ACC CTT CTG CCA AAC AC 3' (SEQ. ID NO. 235) | 5' ATC GAC CGG GAT GCC 3' (SEQ. ID NO. 236) | 243 | GA | 60° C. |
| WMS291 | 5' CAT CCC TAC GCC ACT CTG C 3' (SEQ. ID NO. 237) | 5' AAT GGT ATC TAT TCC GAC CTG AC 3' (SEQ. ID NO. 238) | >158 | CA | 55° C. |
| WMS292 | 5' TCA CCG TGG CCG AC 3' (SEQ. ID NO. 239) | 5' CCA CCG CCA TAA GTT GGT TC 3' (SEQ. ID NO. 240) | 220 | CT | 55° C. |
| WMS293 | 5' TAC TGG TTC ACA TTG GTG CG 3' (SEQ. ID NO. 241) | 5' TCG GCA TCA CTC GTT CAA G 3' (SEQ. ID NO. 242) | 201 | CA | 55° C. |
| WMS294 | 5' GGA TTG AGG TTA AGA GAG AAC CG 3' (SEQ. ID NO. 243) | 5' GCA GAG AGT TCA GGA CCA GA 3' (SEQ. ID NO. 244) | 100 | GAimp | 55° C. |
| WMS295 | 5' GTG AAG CAG ACC CAC TCT AC 3' (SEQ. ID NO. 245) | 5' GGC TGC TGC GAG GAG 3' (SEQ. ID NO. 246) | 258 | GA | 55° C. |
| WMS296 | 5' AAT TCA ACC TAC TCA TCT CTG 3' (SEQ. ID NO. 247) | 5' GCC TAA TAA CTT GAA AAC GAG 3' (SEQ. ID NO. 248) | 149 | CT | 55° C. |
| WMS297 | 5' ATC GTC ACG TAT TTT GCA ATG 3' (SEQ. ID NO. 249) | 5' TCA GTA AGT CTT ACA CTA GC 3' (SEQ. ID NO. 250) | 150 | GT, GA | 60° C. |
| WMS299 | 5' ACT ACT TAG GCC TCC CGC C 3' (SEQ. ID NO. 251) | 5' TGA CCC ACT TGC AAT TCA TC 3' (SEQ. ID NO. 252) | 208 | GA, TAG | 55° C. |
| WMS301 | 5' GAG GAG TAA GAC ACA TGC CC 3' (SEQ. ID NO. 253) | 5' GTG GCT GGA GAT TGT GGT TC 3' (SEQ. ID NO. 254) | 204 | GA, G | 55° C. |
| WMS302 | 5' GCA AGA AAC AGC AGT AGT AAC 3' (SEQ. ID NO. 255) | 5' CAG ATG CTC TCT GCT GG 3' (SEQ. ID NO. 256) | 180 | GA | 60° C. |
| WMS304 | 5' AGG AAA CAG TAT CGC GG 3' (SEQ. ID NO. 257) | 5' AGG ACT GTG GGG AAT GAA TG 3' (SEQ. ID NO. 258) | (340) | CT | 55° C. |
| WMS311 | 5' TCA CGT GGA AGA CGC TCC 3' (SEQ. ID NO. 259) | 5' CTA TGC CAT CCA TAA TGG 3' (SEQ. ID NO. 260) | 217 | CT | 55° C. |
| WMS312 | 5' ATC CGC TGA TGC ACG GTG 3' (SEQ. ID NO. 261) | 5' ACA TGC ATG CAT GCC ATG 3' (SEQ. ID NO. 262) | 151 | GA | 60° C. |
| WMS313 | 5' CCG CCC TTA AGT TTC TTC AC 3' (SEQ. ID NO. 263) | 5' TTT GAC GTC AAG TAC ACG AGT CTG 3' (SEQ. ID NO. 264) | 235 | GA | 60° C. |
| WMS314 | 5' AGG AGC TCC TCT GTG CCA C 3' (SEQ. ID NO. 265) | 5' TGC GTG TGA ACT CTC CCT G 3' (SEQ. ID NO. 266) | 156 | CT, GT | 55° C. |
| WMS316 | 5' CAT GGA CAT TTT ACC ACA AGA C 3' (SEQ. ID NO. 267) | 5' TTC TGC GTG TCC TGT GTT C 3' (SEQ. ID NO. 268) | 170 | CT | 60° C. |
| WMS319 | 5' CGT TGT ACA ACT ATG GAA GTT CAC G 3' (SEQ. ID NO. 269) | 5' CGG GTG CTG CTG GTA GTA AC 3' (SEQ. ID NO. 270) | 176 | AT, GT | 55° C. |
| WMS320 | 5' CGA GAT ATG GAA ATG GTT CAC G 3' (SEQ. ID NO. 271) | 5' ATC TTT GCA AGA ATT GCC C 3' (SEQ. ID NO. 272) | 200 | CT | 55° C. |
| WMS321 | 5' CAA TGT CGA GGT GTG C 3' (SEQ. ID NO. 273) | 5' TGT TGC ATG CGA TCA TGC 3' (SEQ. ID NO. 274) | >263 | GT, GA | 60° C. |
| WMS322 | 5' TCA CAA AAT GAT TTC TCA TCC G 3' (SEQ. ID NO. 275) | 5' TGC AGA AAA CCA ACA AGG G 3' (SEQ. ID NO. 276) | 265 | GT, GAimp | 60° C. |
| WMS325 | 5' TTT CTT CTG GAG TTT TCT TCC C 3' (SEQ. ID NO. 277) | 5' TTT TTA GGT CGT CAG AGA GAC G 3' (SEQ. ID NO. 278) | 119 | GA | 55° C. |
| WMS328 | 5' GCA ATC CTG AGC ACG AAG AG 3' (SEQ. ID NO. 279) | 5' CAC AAA CTC TTG ACA TGT GCG 3' (SEQ. ID NO. 280) | 131 | CT | 55° C. |
| WMS330 | 5' TTG CTA CCA TGC ATG CAG 3' (SEQ. ID NO. 281) | 5' ACA TGT TTC ATG CAG GTA GCC 3' (SEQ. ID NO. 282) | 193 | GT | 55° C. |
| WMS332 | 5' AGC CAG CAA GTC ACC AAA AC 3' (SEQ. ID NO. 283) | 5' AGT GCT GGA AAG AGT AGA GC 3' (SEQ. ID NO. 284) | 165 | GTT | 60° C. |
| WMS333 | 5' GCC CGG TCA TGT AAA ACG 3' (SEQ. ID NO. 285) | 5' TTT CAG TGT GCG TTA AGC TTT G 3' (SEQ. ID NO. 286) | 231 | GA | 60° C. |
| WMS334 | 5' AAT TTC AAA AAG TGA AGA GA 3' (SEQ. ID NO. 287) | 5' AAC ATG TGT TTT TAG CTA TC 3' (SEQ. ID NO. 288) | 150 | GA | 55° C. |
| | | | 123 | GA | 50° C. |

| WMS Number | WMS Primer Left | WMS Primer Right | Length (bp) in "cs" | Repeat Type | Annealing Temperature |
|---|---|---|---|---|---|
| WMS335 | 5' CGT ACT CCA CTC CAC ACG G 3' (SEQ. ID NO. 289) | 5' CGG TCC AAG TGC TAC CTT TC 3' (SEQ. ID NO. 290) | 187 (225) | GA,GCGT | 55° C. |
| WMS336 | 5' CCC TTT AAT CTC GCT CCC TC 3' (SEQ. ID NO. 291) | 5' GTC TCT TAA CTG ACA TTC CAG G 3' (SEQ. ID NO. 292) | 108 | CT | 55° C. |
| WMS337 | 5' CCT TCT CTT CCT TCA CTT AGC 3' (SEQ. ID NO. 293) | 5' TGC TAA CTG ACA ACC ACT CAA TC 3' (SEQ. ID NO. 294) | 183 | CT,CACT,CA | 55° C. |
| WMS339 | 5' AAT TTT CTT TGT CGT TTT ATC C 3' (SEQ. ID NO. 295) | 5' AAA CGA ACA ACC ACT CAA TC 3' (SEQ. ID NO. 296) | 159 | CT | 50° C. |
| WMS340 | 5' GCA ATC TTT TTT CTG ACC ACG 3' (SEQ. ID NO. 297) | 5' ACG AGG CAA CAA CAC ACA TG 3' (SEQ. ID NO. 298) | 132 | GA | 60° C. |
| WMS341 | 5' TTC AGT GGT AGC GGT CGA G 3' (SEQ. ID NO. 299) | 5' CCG ACA TCT CAT GGA TCC AC 3' (SEQ. ID NO. 300) | 133 | CT | 55° C. |
| WMS342 | 5' TAT CCA GAG CAG GAC ACG GAC G 3' (SEQ. ID NO. 301) | 5' GGT CTA GCT TCG ACG ACA CC 3' (SEQ. ID NO. 302) | 169 (150) | GT | 55° C. |
| WMS344 | 5' CAA GGA AAT AGG CGG TAA CT 3' (SEQ. ID NO. 303) | 5' ATT TGA GTC TGA AGT TTG CA 3' (SEQ. ID NO. 304) | 131 | GT | 55° C. |
| WMS346 | 5' CCA GCA AGG TTT CGT TTT ATC C 3' (SEQ. ID NO. 305) | 5' GCA TGT GCT GGT TCT GCC TG 3' (SEQ. ID NO. 306) | 203 | AT,GT | 55° C. |
| WMS349 | 5' GGC TTC CAG AAA ACA ACA GG 3' (SEQ. ID NO. 307) | 5' ATC GGT GCG TAC CAT CCT AC 3' (SEQ. ID NO. 308) | 230 | GA | 55° C. |
| WMS350 | 5' ACC TCA TCC ACA TGT TCT ACG 3' (SEQ. ID NO. 309) | 5' GCA TGG ATA GGA AAG CGC CC 3' (SEQ. ID NO. 310) | 146 | GT | 55° C. |
| WMS353 | 5' CCA TGT TGA GTA GGT TCA GCC 3' (SEQ. ID NO. 311) | 5' CTT GGC CAG AAG CTA CGA AC 3' (SEQ. ID NO. 312) | 179 | GCGT,GT | 60° C. |
| WMS356 | 5' AGC AGT TCT CTT GGG AAT TAG AGA 3' (SEQ. ID NO. 313) | 5' CCA ATC AGT CAT CAA GGA AC 3' (SEQ. ID NO. 314) | 224 | GA | 55° C. |
| WMS357 | 5' TAT GGT CAA AGT TGG ACC TCG 3' (SEQ. ID NO. 315) | 5' ACG CTG CAG CCT TTC TTC AG 3' (SEQ. ID NO. 316) | 123 | GA | 55° C. |
| WMS358 | 5' AAA CAG CGG ATT TCA TCG AG 3' (SEQ. ID NO. 317) | 5' TCC GCT GTT CTG ATC TC 3' (SEQ. ID NO. 318) | 164 | GA | 55° C. |
| WMS359 | 5' GTA ATT GCA GGT CAT GGT GGG 3' (SEQ. ID NO. 319) | 5' TAC TTG TGT TCT GGG ACA ATG G 3' (SEQ. ID NO. 320) | 217 | CT,CTTimp | 55° C. |
| WMS361 | 5' GTA ACT TGT TGC CAA AGG GC 3' (SEQ. ID NO. 321) | 5' ACA AAG ATG GCT TCA AGG ACA 3' (SEQ. ID NO. 322) | 126 | GAimp | 60° C. |
| WMS368 | 5' CCA TTT CAC ATC ATG CCT GC 3' (SEQ. ID NO. 323) | 5' AAT AAA ACC ATG AGC TCA CTT GC 3' (SEQ. ID NO. 324) | 249 | AT | 60° C. |
| WMS369 | 5' CTG CAG GCC ATG ATG G 3' (SEQ. ID NO. 325) | 5' ACC GTG GGT GTT GTA GC 3' (SEQ. ID NO. 326) | 188 | CTimp | 60° C. |
| WMS371 | 5' GAC CAA GAT ATT CAA ACT GGC C 3' (SEQ. ID NO. 327) | 5' AGC TCA GCT TGC GTA CC 3' (SEQ. ID NO. 328) | 170 | CA,GA | 60° C. |
| WMS372 | 5' AAT AGA GCC CTG GGA CTG GG 3' (SEQ. ID NO. 329) | 5' GAA AGA CGA CAT TCC ACC TG 3' (SEQ. ID NO. 330) | >329 | GA | 60° C. |
| WMS374 | 5' ATA GTG TGT TGC ATG CTG TGT G 3' (SEQ. ID NO. 331) | 5' TCT AAT TAG AGC TCG CTG CC 3' (SEQ. ID NO. 332) | 213 | GT | 60° C. |
| WMS375 | 5' ATT GGC GAC TCT AGC AGG TAC G 3' (SEQ. ID NO. 333) | 5' GGG ATG TCT GTT CCA TCT TAG C 3' (SEQ. ID NO. 334) | 156 | CA | 55° C. |
| WMS376 | 5' GGG CTA GAA AAC AGG AAG GC 3' (SEQ. ID NO. 335) | 5' TCT CGT GGA GGG CCA TAG GAG 3' (SEQ. ID NO. 336) | 147 | CA, GAimp | 60° C. |
| WMS382 | 5' GTC AGA TAA CGC CGT CCA AT 3' (SEQ. ID NO. 337) | 5' GAC ATC AAT AAT CGT GGA TGG 3' (SEQ. ID NO. 338) | 115 | GA | 60° C. |
| WMS383 | 5' ACG CAG GTT GAT CCT CTA AAC 3' (SEQ. ID NO. 339) | 5' GCC AAG TTT CTT AGC TAC TAG 3' (SEQ. ID NO. 340) | 195 | GT | 55° C. |
| WMS384 | 5' TTT TCA TTG TGC CCT CTA CT 3' (SEQ. ID NO. 341) | 5' CAC CGC GTC AAC TAC TTA AGC 3' (SEQ. ID NO. 342) | 204 | GTimp | 55° C. |
| WMS388 | 5' CTA CAA TTC GAA GGA GAG GGG 3' (SEQ. ID NO. 343) | 5' CTG CAA CAT TAG CAT ACC AT 3' (SEQ. ID NO. 344) | 162 | CT,CA,CA | 60° C. |
| WMS389 | 5' ATC ATG TCC ATC TTG ACG 3' (SEQ. ID NO. 345) | 5' TGA CAA GTA CAT TAG GGA G 3' (SEQ. ID NO. 346) | 130 | CT,GT | 60° C. |
| WMS390 | 5' AAG TTT CAC ACA AGA TCT CTC C 3' (SEQ. ID NO. 347) | 5' ATG GTC ATG ATG TCG GC 3' (SEQ. ID NO. 348) | 143 | CT,GT | 55° C. |
| WMS391 | 5' ATA GCG AAG TCT CCC TAC TCC A 3' (SEQ. ID NO. 349) | 5' ATG TCG AAT ACA CCT TGC C 3' (SEQ. ID NO. 350) | 150 | CA,GA | 60° C. |
| WMS393 | 5' TCA TCT ATT TGT GCT ACA 3' (SEQ. ID NO. 351) | 5' TCA AAT ACA CCT CCT TG 3' (SEQ. ID NO. 352) | 107 | CA | 55° C. |
| WMS395 | 5' TGT AAC CGC AAG TAA TGC CA 3' (SEQ. ID NO. 353) | 5' TAC CAA CTC CAA CCT TG 3' (SEQ. ID NO. 354) | 147 | CA | 55° C. |
| WMS397 | 5' TGC CAT GGA TTA TTT GGT CGG 3' (SEQ. ID NO. 355) | 5' CTG CAC CAT TAG AGC ATT AG AGC 3' (SEQ. ID NO. 356) | 179 | CT | 55° C. |
| WMS400 | 5' GTG CTG CCA CCA CTT GC 3' (SEQ. ID NO. 357) | 5' TGT AGG CAC TGC TGG AG 3' (SEQ. ID NO. 358) | 139 | CA | 60° C. |
| WMS403 | 5' CGA CAT CTT GGC CTT TG 3' (SEQ. ID NO. 359) | 5' ATA AAA CAG TTC GTT CCA GG 3' (SEQ. ID NO. 360) | 133 | CA | 55° C. |
| WMS408 | 5' GCT TGA GAC TGG AGT 3' (SEQ. ID NO. 361) | 5' GTA TAA CTT GAC CTT AGC AGC ACG C 3' (SEQ. ID NO. 362) | 176 | CA | 55° C. |
| WMS411 | 5' CCC ATA CGA TGA GTT TGT GGT TCC 3' (SEQ. ID NO. 363) | 5' CGA GAC CAT GAT CGT CTT G 3' (SEQ. ID NO. 364) | 334 | CA | 60° C. |
| WMS412 | 5' ATC AAC AAG ATT GAT TGC CCC 3' (SEQ. ID NO. 365) | 5' CAA ATG AAA CGC AAA GCG CCC 3' (SEQ. ID NO. 366) | 148 | CT | 55° C. |
| WMS413 | 5' TGC TTG TTT CCA CCT CGG 3' (SEQ. ID NO. 367) | 5' GAT CAG CGT CTC CTT GGC A 3' (SEQ. ID NO. 368) | 121 | GA | 60° C. |
| WMS415 | 5' GAT CTC CCA TGT CCG CA 3' (SEQ. ID NO. 369) | 5' CGA CAG CCG TCC CTT TA 3' (SEQ. ID NO. 370) | 94 | GA | 55° C. |
| WMS425 | 5' GAG CCC ACA GTG GAT GA 3' (SEQ. ID NO. 371) | 5' TCG TTG TTC CAA GGC TTG 3' (SEQ. ID NO. 372) | 131 | GAimp | 60° C. |
| WMS427 | 5' AAA CTT AGA ACT GTA ATT TCA GA 3' (SEQ. ID NO. 373) | 5' AGT GTG TTC ACT AGC GC 3' (SEQ. ID NO. 374) | >143 | CT | 50° C. |
| WMS428 | 5' CGA GGC AGC GAG GAT T 3' (SEQ. ID NO. 375) | 5' TTC TCC AAG CTA TGA CAG GC 3' (SEQ. ID NO. 376) | 215 | GA | 60° C. |
| WMS429 | 5' TTG TAC ATT AAG TTC CCA TTA 3' (SEQ. ID NO. 377) | 5' TTT AAG GAC CTA CAT GAC AC 3' (SEQ. ID NO. 378) | 143 | CA | 50° C. |
| | | (SEQ. ID NO. 379) | 221 (290) | CT | |
| | | (SEQ. ID NO. 380) | | | |

-continued

| WMS Number | WMS Primer Left | WMS Primer Right | Length (bp) in "cs"* | Repeat Type | Annealing Temperature |
|---|---|---|---|---|---|
| WMS434 | 5' ATG AGT TCC GCC AAA GAA TG 3' (SEQ. ID NO. 381) | 5' ACG AAA TAC ACA AGT GGG ACA 3' (SEQ. ID NO. 382) | 216 | GT | 55° C. |
| WMS437 | 5' GAT CAA GAC TTT TGT ATC TCT C 3' (SEQ. ID NO. 383) | 5' GAT GTC CAA CAG CTT TA 3' (SEQ. ID NO. 384) | 109 | CT | 50° C. |
| WMS440 | 5' CCT ATG GTC TCC ATC ATG AGG 3' (SEQ. ID NO. 385) | 5' TCA TGT CAA CTC AAG ACG 3' (SEQ. ID NO. 386) | 112 | CT | 55° C. |
| WMS443 | 5' GGG TCT TCA TCC GGA ACT CT 3' (SEQ. ID NO. 387) | 5' CCA TGA TTT ATA AAT TCC ACC 3' (SEQ. ID NO. 388) | 134 | CA,GA | 55° C. |
| WMS445 | 5' TTT GTT GGG GGT TAG GAT TAG 3' (SEQ. ID NO. 389) | 5' CCT TAA CAC TTG CTG GTA GTG 3' (SEQ. ID NO. 390) | 192 | CT | 55° C. |
| WMS448 | 5' AAA CCA TAT TGG GAG GAA AGG 3' (SEQ. ID NO. 391) | 5' CAC ATG GCA TCA CAT TTG TG 3' (SEQ. ID NO. 392) | 231 | GA | 60° C. |
| WMS455 | 5' ATTT CGG TTC GCT AGC TAC CA 3' (SEQ. ID NO. 393) | 5' ACG AAC AAC CTG CC 3' (SEQ. ID NO. 394) | 151 | GTimp | 55° C. |
| WMS456 | 5' TCT GAA CAT TAC ACA ACC CTG A 3' (SEQ. ID NO. 395) | 5' TGC TCT CTC TGA ACC TGA AGC 3' (SEQ. ID NO. 396) | 132 | GA | 55° C. |
| WMS458 | 5' AAT GGC AAT TGG AAG ACA TAG C 3' (SEQ. ID NO. 397) | 5' TTC GCA ATG TTG ATT TGG C 3' (SEQ. ID NO. 398) | 113 | CA | 60° C. |
| WMS459 | 5' ATG GAG TGG TCA CAC TTT GAA 3' (SEQ. ID NO. 399) | 5' AGC TTC TCT GAC CAA CTT CTC G 3' (SEQ. ID NO. 400) | >138 | GA | 55° C. |
| WMS469 | 5' CAA CTC AGT GCT CAC ACA ACG 3' (SEQ. ID NO. 401) | 5' CGA TAA CTC ATC ATC CAC ACC 3' (SEQ. ID NO. 402) | >156 | CT | 60° C. |
| WMS471 | 5' CGG CCC TAT CAT GGC TG 3' (SEQ. ID NO. 403) | 5' GCT TGC AAG TTC CAT TTT GC 3' (SEQ. ID NO. 404) | 149 | CA | 60° C. |
| WMS473 | 5' TCA TAC GGG TAT GGT TGG AC 3' (SEQ. ID NO. 405) | 5' CAC CCC CTT GTT GGT CAC 3' (SEQ. ID NO. 406) | 220 | GTimp | 55° C. |
| WMS476 | 5' ATG GGT TCG TAC CAT CAG C 3' (SEQ. ID NO. 407) | 5' TTG CTG GTA GCT ATC CC 3' (SEQ. ID NO. 408) | >194 | GTimp | 60° C. |
| WMS480 | 5' TGC TGC TAC TTG GCT AGA GGA C 3' (SEQ. ID NO. 409) | 5' CCG AAT TGT CCG CCA TAG 3' (SEQ. ID NO. 410) | 188 | CT,CA | 60° C. |
| WMS484 | 5' ACA TCG CTC TTC ACA AAC CC 3' (SEQ. ID NO. 411) | 5' AGT TCC GGT CAT GGC TAG G 3' (SEQ. ID NO. 412) | 145 | CT | 55° C. |
| WMS494 | 5' ATT GAA CAG GAA GAC ATC AGG G 3' (SEQ. ID NO. 413) | 5' CAC CTG GAG CTG TCT GGC 3' (SEQ. ID NO. 414) | 198 | CA | 60° C. |
| WMS495 | 5' GAG AGC CTC GCG AAA TAT AGG 3' (SEQ. ID NO. 415) | 5' TGC TTC TGG TGT TTC G 3' (SEQ. ID NO. 416) | 168 | GA | 60° C. |
| WMS497 | 5' GTA GTG AAG ACA AGG GCA TTG 3' (SEQ. ID NO. 417) | 5' CCG AAA GTT GGG TGA TAT AC 3' (SEQ. ID NO. 418) | >106 | GTimp | 55° C. |
| WMS499 | 5' ACT TGT ATG CTC CAT TGA TTG C 3' (SEQ. ID NO. 419) | 5' GGG GAG TGG AAA CTG CAT AA 3' (SEQ. ID NO. 420) | 145 | GA | 60° C. |
| WMS501 | 5' GGC TAT CTC TGG CGC CAA AA 3' (SEQ. ID NO. 421) | 5' TCC ACA AAC AAG TAG CGC C 3' (SEQ. ID NO. 422) | 172 | CA | 55° C. |
| WMS512 | 5' AGC CAC CAT CAG CAG AAA TT 3' (SEQ. ID NO. 423) | 5' GAA CAT GAG CAG TTT GGC AC 3' (SEQ. ID NO. 424) | 185 | GT | 60° C. |
| WMS513 | 5' ATC CGT AAG ACC TAC TGG TCA 3' (SEQ. ID NO. 425) | 5' CCG AAT TGT CCG CCA TAG 3' (SEQ. ID NO. 426) | 144 | CA | 60° C. |
| WMS515 | 5' AAC TCG ACA ATG GCA ATG AGA 3' (SEQ. ID NO. 427) | 5' GGT CTG TTC ATG CCG CAT GT 3' (SEQ. ID NO. 428) | 134 | GTimp | 60° C. |
| WMS518 | 5' AAT CAC CAG AAG ACG TGA CA 3' (SEQ. ID NO. 429) | 5' CCT TCC TAG TAA GTG TGC CTC A 3' (SEQ. ID NO. 430) | 166 | CA | 55° C. |
| WMS530 | 5' AAA TAG GAC AAC CCA CGG C 3' (SEQ. ID NO. 431) | 5' CAG GGT GGT GCA TGC AT 3' (SEQ. ID NO. 432) | 186 | CT | 55° C. |
| WMS532 | 5' ACT GCG TGT GCC TAC AAT TG 3' (SEQ. ID NO. 433) | 5' TCA ACT TCT TGG CCT CCA TC 3' (SEQ. ID NO. 434) | 142 | GT | 55° C. |
| WMS533 | 5' AAG GCG AAT CTT GTC ACC GAA TA 3' (SEQ. ID NO. 435) | 5' AGG AGT CCA CTT CAA AAT T 3' (SEQ. ID NO. 436) | 167 | CT,ATCT,CT | 55° C. |
| WMS537 | 5' ACA TAA TGC TTC CTG TGC ACC 3' (SEQ. ID NO. 437) | 5' GTT GCT TTA CTC GAT AGG CC 3' (SEQ. ID NO. 438) | 147 | CT, CA | 55° C. |
| WMS538 | 5' GCA TTT CGG GTG AAC CC 3' (SEQ. ID NO. 439) | 5' GCC ACT TTT GTG TCG CTT CT 3' (SEQ. ID NO. 440) | 209 | CA,TA | 60° C. |
| WMS540 | 5' TCT CGC TCT ATC CTA TTT C 3' (SEQ. ID NO. 441) | 5' GTT GCA TGT GCT CGT TAA GCG G 3' (SEQ. ID NO. 442) | 147 | GTimp | 60° C. |
| WMS544 | 5' TAG AAT TCT TTA TGG TGC AAT TG 3' (SEQ. ID NO. 443) | 5' AGG CAT ATT CCA ATC CTT CAA AAT T 3' (SEQ. ID NO. 444) | 129 | CTimp | 55° C. |
| WMS550 | 5' CCC ACA AGA ACC TTT GAA GA 3' (SEQ. ID NO. 445) | 5' CAT TGT GTG ACC ATG GCA C 3' (SEQ. ID NO. 446) | 150 | CT, GT | 55° C. |
| WMS554 | 5' TGC CCA TCA CGG AAC TTG 3' (SEQ. ID NO. 447) | 5' GCA ACC ACC TTA GCC AAA GT 3' (SEQ. ID NO. 448) | 160 | CT,GTimp | 60° C. |
| WMS565 | 5' GCG TCA TAC ATG CCT ACC TAG G 3' (SEQ. ID NO. 449) | 5' AGT GCT TCG AGG TAA GCC A 3' (SEQ. ID NO. 450) | 142 | CA | 60° C. |
| WMS566 | 5' TCT GCC TAC TGG TCA TGG TG 3' (SEQ. ID NO. 451) | 5' CTG ACG TCG ACA GAA GAA TT 3' (SEQ. ID NO. 452) | 130 | CA,TA | 60° C. |
| WMS569 | 5' GGA AAC TTA TTG ATT GAA AT 3' (SEQ. ID NO. 453) | 5' TCA ATT TTT ACA GAA CCA TT 3' (SEQ. ID NO. 454) | 134 | GT | 47° C. |
| WMS570 | 5' TCG CCT TTT ACA GTC GGC 3' (SEQ. ID NO. 455) | 5' ATG GGT AGC TGA GAG CCA AA 3' (SEQ. ID NO. 456) | 143 | CT,GT | 60° C. |
| WMS573 | 5' AAG AGA TAA TTT GGT GAA GAA AA 3' (SEQ. ID NO. 457) | 5' TTC AAA TAT GTG GGA ACT TAT 3' (SEQ. ID NO. 458) | 212 | CA | 50° C. |
| WMS577 | 5' ATG AGG CTC TGT GGA GAA ATT G 3' (SEQ. ID NO. 459) | 5' TGT TTC AAG CCC GTT TCA TA T 3' (SEQ. ID NO. 460) | 133 | CA,TA | 55° C. |
| WMS582 | 5' AAG CAC TAA TTT GAA AAT ATG AC 3' (SEQ. ID NO. 461) | 5' TCT TAA GGT GTT TTA TCA TA 3' (SEQ. ID NO. 462) | 151 | CA | 50° C. |
| WMS583 | 5' TTC ACA CCC AAC AAC CAA CA 3' (SEQ. ID NO. 463) | 5' TCT AGG CAG ACA CAT GCC TG 3' (SEQ. ID NO. 464) | 165 | CA | 60° C. |
| WMS588 | 5' GAT CCC CAA TTG CAT GTT G 3' (SEQ. ID NO. 465) | 5' CTT GCA ACT GGG GGA CAC 3' (SEQ. ID NO. 466) | 102 | GT | 60° C. |

*"CS" Weizensorte 'Chinese Spring'

These markers are distinguished by a high degree of polymorphism between different wheat varieties or lines and usually detect several alleles per genetic locus in different wheat lines.

They can therefore be used for DNA fingerprinting, species identification, relationship or similarity studies, characterization of cytological lines, such as deletion lines, substitution lines, addition lines, etc. and all forms of genetic mapping, including mapping of individual genes and quantitative trait analysis features (QTLs). In addition, their use is also very suitable for automation and it is possible to carry out the detection of the products with nonradioactive methods.

With the help of these inventive markers the possibility is provided, for example, of differentiating almost all European wheat lines.

The invention is described in greater detail below by means of examples.

1. Amplification of the Microsatellite Markers

The microsatellite markers are amplified according to the following protocol:
10 mM tris-HCl, pH 8 50 mM KCl 1.5 mM MgCl$_2$ (in a few exceptional cases 3 mM MgCl$_2$) 0.01% (w/v) gelatin 0.2 mM of each desoxynucleotide 250 nM of each primer (in each case to the left and right of a pair) 1–2 units taq polymerase 50–150 ng matrixes (template) DNA
are amplified in a volume of 25 or 50 IL according to the following profile:

| | | |
|---|---|---|
| 92° C. | 3 minutes | |
| 92° C. | 1 minute (denaturing phase) | |
| 60° C. | 1 minutes (annealing phase) | 45 cycles |
| 72° C. | 2 minutes (elongation phase) | |
| 72° C. | 10 minutes (extension phase) | |

The amplification takes place in a Perkin Elmer 9600 with lid heating or in an MJ Research Thermocycler without lid heating. In this apparatus, a layer of mineral oil is placed over the reactions. The temperature of the annealing phase depends on the melting point (Tm) of the primer and in some cases is 50° C or 55° C.

2. Separation of the Microsatellite Markers on Polyacrylamide Gels, Which Are Not Denaturing The PCR reactions are mixed with 1/10 volume of stop buffer (0.02 M tris acetate of pH 8.1, 0.025 M sodium acetate, 0.02 M EDTA, 70% glycerin, 0.2% SDS, 0.6% bromphenol blue, 0.6% xylene cyanol) and in each case 25 µL are separated in 10% polyacrylamide gels (1.5 mm thick, 18 cm long).

Formulation for polyacrylamide gel (10%):

| | |
|---|---|
| 25 mL | stock acrylamide solution (19 g acrylamide, 1 g bisacrylamide, diluted to 100 mL with water) |
| 10 mL | 5X TBE (1X TBE = 0.09 M tris borate of pH 8.3, 0.002 M EDTA |
| 15 mL | water | are mixed and the polymerization is started by the addition of 220 µL of ammonium persulfate (10%, freshly prepared) and 20 µL of TEMED. Immediately after the addition, the mixture is poured into the sealed gel mold and the comb for forming pockets is inserted. The polymerization is completed after about 1 hour. The gel is placed in the gel chamber and a preliminary run is carried out without samples for about 30 minutes at 150 volts in IX TBE. After that, the samples are loaded (25 µL of each) and the separation is carried out for 14–16 hours at 100 volts.

After the electrophoresis is completed, the gel is stained in ethidium bromide (1–2 drops of 10 mg/mL in 1 liter of water) and the fragments are made visible by a UV transilluminator and documented.

3. Separation of Microsatellite Markers on Denaturing Gels

For the separation of the amplified fragments on denaturing gels, an automatic laser fluorescence (A.L.F.) sequencer (Pharmacia), for example, is used. In order to enable the fragments to be detected by means of a laser, one primer per pair is marked at the 5' end with fluorescein. Per PCR reaction, 0.3 to 1.5 microliters are mixed with 2.5 microliters of stop buffer (deionized formamide; 5 mg/mL dextran blue), denatured (1 minute; 90° C.) and loaded onto the gel. Gel plates with a 9 cm separation distance are used, as recommended by the manufacturer for the fragment analysis. The gel solution contains 6.5% Long-Ranger (AT Biochem), 7M urea and 1.2X TBE buffer. The gels are 0.35 or 0.5 mm thick. The conditions for the gel run are 600 V, 40 mA, 50 W, 0.84 s data collection interval and 2 mW laser energy. The gel runs are ended after about 80 to 90 minutes. This is sufficient for detecting fragments up to a size of 300 bp. A gel can be used for four or five runs. For each gel run, a data set is obtained. With this data and by means of internal size standards, the exact fragment sizes sre determined in the computer program Fragment Manager (Pharmacia) and thus the smallest size differences of a base pair are deterrnined.

What is claimed is:

1. A method of genotyping plants of the Triticum aestivum species and the genus Triticeae at a microsatellite locus, the method comprising a) amplifying chromosomal DNA with one or more oligonucleotide primer pairs specifically hybridizing to said locus of a region of said chromosomal DNA, wherein said region of the DNA comprises a repeated dinucleotide motif comprising at least one of the following selected from the group consisting of $(GA:CT)_n$, $(GT:CA)_n$, $(AT:TA)_n$, where $n \geq 10$, to obtain an amplification product, b) wherein each primer pair consists of a first oligonucleotide of SEQ ID NO. x and a second oligonucleotide of SEQ 10 NO. x+1, and wherein x=1, 3, 5, 7, 9, 11, 13, 15, 17, 19; and c) size fractionating the amplification product to provide a measure of the said motif of the chromosomal DNA between said primer pairs, wherein the size of the amplification product is polymorphic for said locus and provides a marker for genotyping said plants.

2. The method of claim 1, further comprising the step of using the resulting genotype for a further step chosen from the group consisting of DNA fingerprinting, species identification, relationship studies, similarity studies, characterization of cytological lines, and genetic mapping.

3. The method of claim 1, further comprising one or more primer pairs, wherein said primer pairs hew a first oligonucleotide of SEQ ID NO: x and a second oligonucleotide of SEQ ID NO: x+1, and wherein x=93, 129, 203, 277, 345, 381, 397, 425, 435, and/or 445.

* * * * *